(12) United States Patent
Jendralla et al.

(10) Patent No.: US 7,563,888 B2
(45) Date of Patent: Jul. 21, 2009

(54) PROCESS FOR THE PREPARATION OF DIPHENYL AZETIDINONE DERIVATIVES

(75) Inventors: Joachim-Heiner Jendralla, Frankfurt (DE); Guenter Billen, Niedernhausen (DE); Wendelin Frick, Hunstetten-Beuerbach (DE); Bernd Junker, Bad Soden (DE); Theodor Andreas Wollman, Hattersheim (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 11/557,310

(22) Filed: Nov. 7, 2006

(65) Prior Publication Data

US 2007/0149501 A1 Jun. 28, 2007

Related U.S. Application Data

(63) Continuation of application No. PCT/EP2005/005497, filed on May 20, 2005.

(30) Foreign Application Priority Data

May 21, 2004 (DE) .................. 10 2004 025 072

(51) Int. Cl.
- C07D 205/08 (2006.01)
- C07D 307/20 (2006.01)
- C07F 7/18 (2006.01)
- C07C 237/20 (2006.01)
- C07C 235/38 (2006.01)

(52) U.S. Cl. .................. 540/200; 549/475; 556/419; 564/165

(58) Field of Classification Search .............. 540/200; 556/419; 564/165; 549/419, 475
See application file for complete search history.

(56) References Cited

FOREIGN PATENT DOCUMENTS

EP 0524595 1/1993

OTHER PUBLICATIONS

Jose L. Vicario, Dolores Badia, and Luisa Carrillo J. Org. Chem.; 2001; 66(26) pp. 9030-9032.*

* cited by examiner

*Primary Examiner*—Mark L Berch
(74) *Attorney, Agent, or Firm*—Jiang Lin; Craig M. Bell

(57) ABSTRACT

The present invention is a process for the preparation of diphenylazetidinone derivatives of the formula (I) or forms thereof comprising the substituents X, $R^1$ and/or $R^2$ as defined herein. More specifically, the invention comprises methods for the preparation of these compounds by cyclization of certain β-amino carboxamides or β-amino carboxylic esters. These diphenylazetidinone compounds are useful in the treatment of high blood serum cholesterol levels and the maintenance of the reduced cholesterol levels achieved thereby.

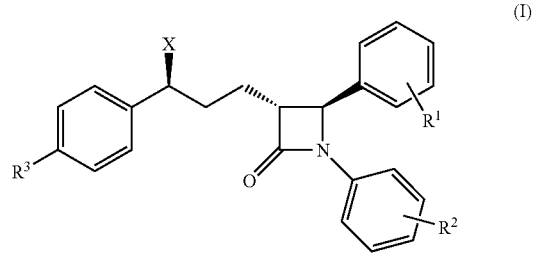

(I)

7 Claims, No Drawings

PROCESS FOR THE PREPARATION OF DIPHENYL AZETIDINONE DERIVATIVES

CROSS-REFERENCE TO RELATED APPLICATIONS

This application is a continuation of International Application No. PCT/EP2005/005497 filed on May 20, 2005 which is incorporated herein by reference in its' entirety which also claims the benefit of priority of German Patent Appln. No 10 2004 025 072.3 filed on May 21, 2004.

FIELD OF THE INVENTION

The invention relates generally to the preparation of cholesterol-lowering agents and pharmaceutical compositions containing them. More specifically, the present invention relates to a process for the preparation of 1,4-diphenyl azetidinone derivatives and compositions containing them for the treatment of high blood serum cholesterol levels and the maintenance of lower levels over time. More specifically, the invention comprises methods for the preparation of these compounds by cyclization of certain β-amino carboxamides or β-amino carboxylic esters.

BACKGROUND OF THE INVENTION

Ezetimibe is a known representative of these compounds which blocks the absorption of cholesterol from the intestine, so that both lower LDL levels and fewer triglycerides are observed in patients. Specifically, the compound is 1-(4-fluorophenyl)-3(R)-[3-(4-fluorophenyl)-3(S)-hydroxypropyl]-4(S)-(4-hydroxyphenyl)-2-azetidinone of the following formula (see claim 8 in EP 0 720 599 B1).

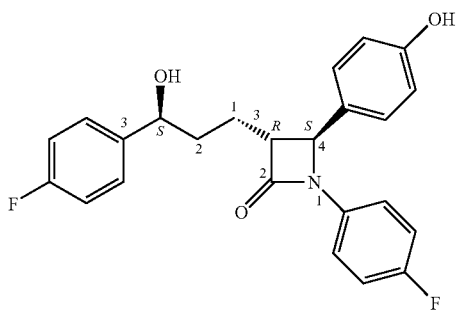

Knowing this compound per se, there are also known to exist some chemical modifications, as well as their preparation by various process variants and their therapeutic use for the treatment of hyperlipidemia and of arteriosclerosis and hypercholesterolemia, inter alia the following publications have appeared, attempts having been made for example to define chemical modifications of comparable therapeutic effect but with less intestinal absorption.

EP 0 524 595 A1 describes chemical modifications of ezetimibe of the formula

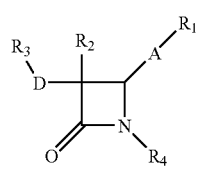

which may inter alia also have a second substituent ($R_2$) in position 3 of the azetidinone ring, also have connecting moieties (A) between the phenyl ring in position 4 of the azetidinone ring and the ring, and have no or other substituents instead of the fluorine groups on the phenyl rings ($R_3$, $R_4$).

The compounds are synthesized (e.g. for $R_2$=H) either by cyclization of hydroxy amides of the formulae

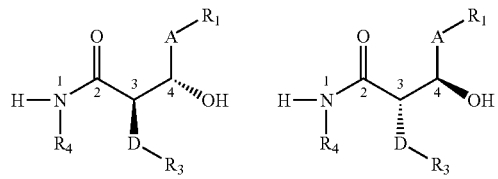

with, for example, trialkylphosphine/dialkyl azodicarboxylate, a phase-transfer catalyst, dialkyl chlorophosphate/tetra-n-butylammonium hydrogen sulfate or dichlorobenzoyl chloride/NaH, or by reaction of esters ($R_x$ is, for example alkyl) of the following formula with imines in the presence of strong bases

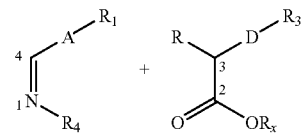

or by a comparable reaction, but with a different carboxylic acid derivative, e.g. an acid chloride or mixed anhydride (in which case 2-oxy-N-methylpyridinium iodide for example instead of $OR_x$), or by modifying the preparation of the above hydroxy amides in the (precursor) stage of the compound of the formula

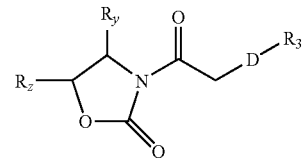

($R_y$, $R_z$ are, for example, independently of one another H, ($C_1$-$C_6$)alkyl, phenyl, benzyl) by reaction with one of the imines $R_1$-A-CH=N—$R_4$ defined above in the presence of $TiCl_4$ and TMEDA (tetramethylethylenediamine) to give

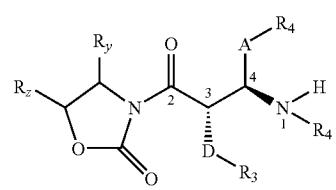

and further reaction with Na bis-trimethylsilylamide or Li bis-trimethylsilylamide to give

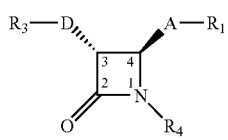

EP 0 707 567 B1 discloses a specific process for preparing azetidinone derivatives of this type in which (Q=H or, for example, alkyl)

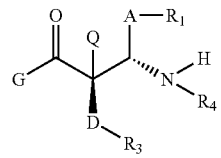

β-(substituted amino) imides of the above formula, which are protected in a suitable way, where G- is selected from the group comprising one of the following radicals,

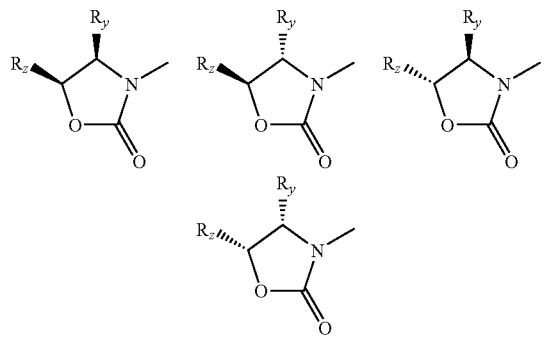

which are reacted with a silylating agent and a fluoride ion catalyst as a cyclizing agent or with a salt of the chiral compound (G⁺ salt), in particular with bis(trimethylsilyl)acetamide and tetra-n-butylammonium fluoride.

Further compound modifications of diphenylazetidinone derivatives are described for example in WO 02/50027 which is hereby incorporated by reference, wherein at least one of the substituents on the three (3) phenyl radicals present in the molecule is a ($C_1$-$C_{30}$)alkylene-(LAG) radical in which one or more carbon "C" atoms of the alkylene radical may be replaced by, for example, —O—, —CH=CH— or —NR— [R=H, ($C_1$-$C_6$)alkyl, ($C_1$-$C_6$)alkylene-phenyl], and LAG is for example a saccharide, disaccharide, trisaccharide, amino acid or oligopeptide residue.

One disadvantage of this process is the use of large amounts of silylating agents such as N,O-bis(trimethylsilyl) acetamide, because acetamide is produced during the reaction and is classified as carcinogenic. In addition, the diastereoselectivity during the addition reaction stage by using enolate and imine tends to be moderate, making additional separation stages necessary.

It is an object of the invention to indicate a further synthesis variant for the aforementioned compounds, which can also be carried out stereospecifically and in high yield, by requiring auxiliary reagents which have minimal toxicity so that it does not give rise to major problems at the workplace when also implemented industrially.

SUMMARY OF THE INVENTION

The present invention is a process for the preparation of diphenylazetidinone derivatives of the formula (I) or forms protected in the substituents X, $R^1$ and/or $R^2$ as defined herein. More specifically, the invention comprises methods for the preparation of these compounds by cyclization of certain β-amino carboxamides or β-amino carboxylic esters. These diphenylazetidinone compounds are useful in the treatment of high blood serum cholesterol levels and the maintenance of the reduced cholesterol levels achieved thereby.

DETAILED DESCRIPTION OF THE INVENTION

One aspect of the present invention then is a process for preparing diphenylazetidinone derivatives of the formula (I)

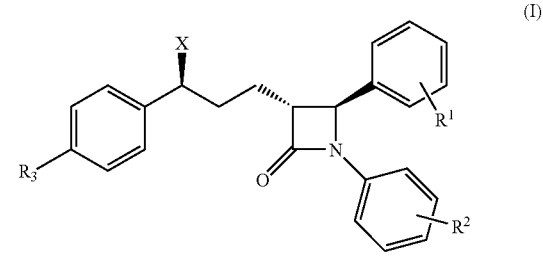

(I)

in which the symbols, substituents and indices have the following meanings:
X=H, OH
$R^1$=OH, $OCH_3$
$R^2$=F, $CH_2CH_3$, $CH_2NHR^4$
$R^3$=H, F
$R^4$=H, CO—$(CH_2—)_n$CO—$R^5$, CO—$(CH_2—)_n$$NHR^6$
n=integers from 4 to 16
$R^5$=OH, NH—$CH_2$—[CH(OH)—$]_m$$CH_2OH$
$R^6$=H, CO—[CH(OH)—$]_m$$CH_2OH$
m=integers from 1 to 5 in which compounds of the formula (II)

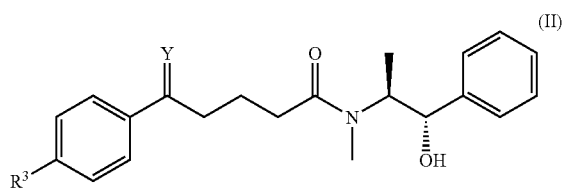

(II)

Wherein Y=H, H; H, OH; H, OAc; H, OSi(alkyl)$_o$(aryl)$_p$ with o, p=0, 1, 2 or 3 and o+p=3; H, OTHP (THP is the tetrahydropyranyl protective group); H, OC(aryl)$_3$; H, OCH$_2$Oalkyl; H, OCH(Oalkyl)CH$_3$; H, Oalkyl; H, OCH$_2$aryl; O-alkyl, O-alkyl; cyclic ketal such as O—(CH$_2$—)$_q$—O with q=2 or 3 with imines of the formula (III)

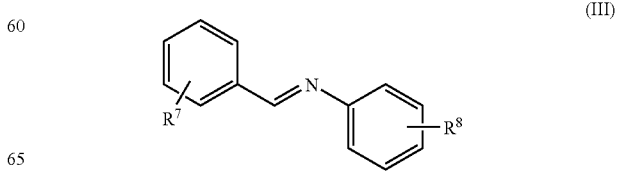

(III)

wherein,

R⁷=R¹ and additionally an O-protective group
R⁸=R², CH₂N[Si(alkyl)ₒ(aryl)ₚ]CO₂CH₂(C₆H₅),
CH₂N[Si(alkyl)ₒ(aryl)ₚ]CO₂tert-butyl,
CH₂N=CH(C₆H₅), CH₂N=CH(C₆H₄-pOCH₃),
CH₂N=CH[C₆H₄(R⁴)] and

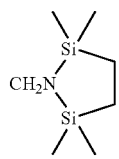

resulting in the intermediates of the formula (IV)

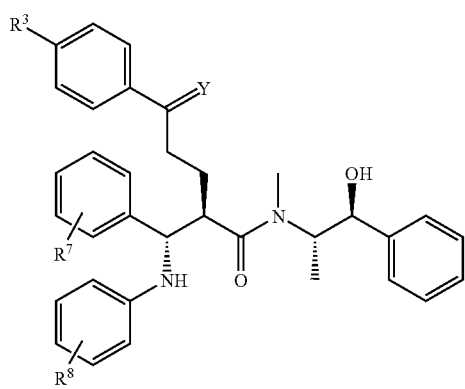

(IV)

after which these amino amides of the formula (IV) are converted where appropriate into esters, mixed anhydrides or active esters of the formula (V)

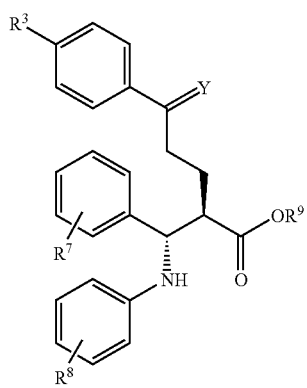

(V)

with possible intermediate production of the carboxylic acid with R⁹=H, and where R⁹ is (C₁-C₄)alkyl, CO(C₁-C₄)alkyl, COO(C₁-C₄)alkyl, SO₂aryl, and after which subsequently the compounds of the formula (IV) or where appropriate (V) are cyclized to give the lactam of the formula (VI)

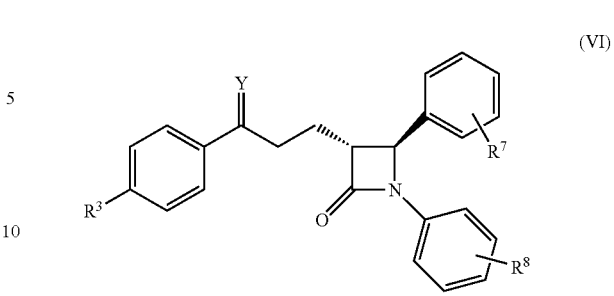

(VI)

and where appropriate finally the compounds of the formula (VI) are deprotected and/or reacted to give the compounds of the formula (I).

A reaction sequence which is to be quoted as typical—including the precursors—is described below by way of example. Methyl 5-(4-fluoro-phenyl)-5-oxopentanoate (VII) can be prepared from fluorobenzene as described in Tetrahedron (Volume 49, pages 3193-3202, 1993).

In the following step, the keto group is reduced by means of a chiral reducing agent to the alcohol (VIII), the S enantiomer. All methods known to the skilled worker can be employed in this case. Examples thereof are (R)-methyl-CBS-catalyzed reduction with borane-dimethyl sulfide complex or borane-tetrahydrofuran complex (see, for example, WO 00/34240) and ruthenium(II)-catalyzed asymmetric hydrogenation (analogous to J. Am. Chem. Soc. 1996, 118, 2521 to 2522). It has additionally been found that the enantioselective hydrosilylation catalyzed by a chirally complexed copper(I) hydride [for the principle, see B. Lipshutz et al, J. Am. Chem. Soc. 2003, 125, 8779 to 8789] can also be used.

This asymmetric hydrosilylation has, in the precursor situation [δ-keto ester (VII), herein after] specifically present in the process of the invention, and from the viewpoint of feasibility, environmental compatibility and economics on the industrial scale, a number of advantages compared with the oxazaborolidine-catalyzed reduction with borane complexes and compared with the asymmetric hydrogenation. The preferred reducing agent poly(methylhydrosiloxane)=(PMHS) is very favorably priced on the industrial scale (cheapest known silane), has low volatility (boiling point >177° C.), is non-hazardous when handled and has good environmental compatibility. In contrast thereto, the borane-THF or -DMS complex is distinctly more costly, has substantially greater volatility, safe industrial handling requires some expenditure, and the substances are considerable environmental pollutants. The use of the borane complexes in production requires, for example, a continuous exhaust air incineration system because both the borane itself and the dimethyl sulfide are extremely malodorous. In addition, the reduction with borane complexes is accompanied by the formation of hydrogen during the various phases of the reaction and work up procedure. To avert the possibility of oxygen/hydrogen explosions occurring in the pipes leading to the exhaust air incineration system it is necessary continuously to feed in large amounts of nitrogen for reliable prevention of the explosive limit being reached. In addition, the commercial (R)-methyl-CBS solution is costly and the reaction is only moderately catalytic.

The classical Corey procedure as used herein after in Example 1 of the present application typically requires 2 to 5 mol % of the oxazaborolidine catalyst, i.e. it takes place with a substrate/catalyst ratio of 20 to 50:1 (S/C=20:1 to 50:1). No examples with S/C>100 are described in the literature on CBS-catalyzed reductions. By contrast, Examples 32 and 33 prove that the alcohol (VIII) is obtained in high chemical and optical yield with ligands such as BINAP in the asymmetric hydrosilylation by the Lipshutz method with a substrate/ligand ratio of 3660 (S/L=3660).

A further advantage is that the asymmetric hydrosilylation takes place at high concentration in toluene as solvent (see Examples 32 and 33), whereas the CBS reduction is normally carried out at higher dilution and in industrially less desirable solvents such as dichloromethane or THF.

The advantage of the asymmetric hydrosilylation compared with Noyori's asymmetric Ru(II)-catalyzed hydrogenation (R. Noyori et al, J. Am. Chem. Soc. 2003, 125, 13490; J. Am. Chem. Soc. 2002, 124, 6508; Angew. Chem. 2001, 113, 40) is mainly that the catalyst costs are low. The asymmetric hydrosilylation proceeds via a chirally complexed CuH catalyst which is produced in situ from a low-cost copper(I) salt (e.g. CuCl), the ligand and the silane, preferably PMHS, in the reaction solvent (e.g. toluene). To this extent, the catalyst costs, irrespective of the S/C ratio achieved, are of only minor importance as long as the S/L ratio is acceptably high. In contrast thereto, the ruthenium precatalyst for the asymmetric Noyori hydrogenation of a non-chelating aryl ketone is prepared from a suitable ruthenium(II) compound, an optically pure diamine and an optically pure diphosphane. Each of these three components and the preparation of the precatalyst are costly.

Synthesis of δ-hydroxy pseudoephedrine amides of the formula (II) [Y=H, OH] via asymmetric hydrosilylation of the keto group of suitable δ-keto esters, e.g. (VII), is thus one of the preferred embodiments of the present invention.

The asymmetric hydrosilylation can be carried out in the temperature range from −78 to +30° C., preferably at −50° C. to +10° C., particularly preferably at −20° C. to 0° C. All aprotic solvents which are inert towards the silane employed can be employed in principle, with preference for the class of ethers, and chlorinated, saturated or aromatic hydrocarbons, particularly preferably toluene, THF, fluorobenzene, chlorobenzene, dichloromethane, cyclohexane, heptane or pentane, especially toluene. The (above-) stoichiometric reducing agent is a silane such as polymethylhydrosiloxane (PMHS), diphenylmethylsilane ($Ph_2MeSiH$), diphenylsilane ($Ph_2SiH_2$), phenylsilane ($PhSiH_3$), tetramethyldisiloxane (TMDS), tert-butyldimethylsilane (TBS-H), triethylsilane (TES-H), preferably PMHS, $Ph_2MeSiH$ or TMDS, particularly preferably PMHS. The silane is employed in excess based on the precursor, preferably 1.2 to 6.0 equivalents, particularly preferably 2.0 to 5.0 equivalents.

The catalytically active species is probably a chelate complex of copper(I) hydride with a chiral diphosphane. This catalytic species is preferably generated in situ in the reaction mixture from a suitable copper compound, a strong base, a chelating chiral diphosphane and the silane. It is preferred to employ as copper compound CuCl, $CuCl_2$, $CuF_2$, or Stryker's reagent [($PPh_3$)CuH]$_6$, particularly preferably CuCl or Stryker's reagent. The copper compound is employed in an amount of from 0.01 mol % to 10 mol % based on the precursor (ketone), preferably in an amount of from 0.1 mol % to 3 mol %, particularly preferably in an amount of from 0.5 mol % to 1.0 mol %.

The strong base is preferably an alkali metal alcoholate or alkali metal hexamethyldisilazane, particularly preferably sodium tert-butanolate, sodium methanolate or NaHMDS. The base is employed either equimolar or in excess relative to the copper compound, preferably 1.0 to 10.0 equivalents, particularly preferably 1.0 to 6.0 equivalents, based on the copper compound.

The ligand employed is a chiral, chelating diphosphane, it often being the case that the enantioselectivity of the catalytic hydrosilylation and the productivity of the catalyst is higher when the dihedral angle in the chiral diphosphane is smaller. Preferred ligands are derived from the diphosphane classes BINAP, DuPHOS, FerroTANE, JOSIPHOS, WALPHOS, BITIANP, BIPHEMP, MeO-BIPHEP and SEGPHOS. Particularly preferred ligands are BINAP, $Cy_2$ PF-$PCy_2$, BITIANP, 5-Xyl-MeO-BIPHEP, 4-MeO-3,5-DTBM-MeO-BIPHEP, DM-SEGPHOS, DTBM-SEGPHOS, very particularly preferably 5-Xyl-MeO-BIPHEP, 4-MeO-3,5-DTBM-MeO-BIPHEP, DM-SEGPHOS, DTBM-SEGPHOS.

The ratio of substrate (ketone) to ligand (chiral diphosphane) is S/L=100 to 500 000, preferably 500 to 100 000, particularly preferably 5000 to 50 000. Whereas chelation by the diphosphane ligand stabilizes the CuH species, the free, uncomplexed portion of the CuH is thermally unstable. In the particularly preferred temperature range from −20° C. to 0° C. it is therefore possible frequently to observe gradual, progressive decomposition of the free portion of CuH to form black particles during reaction times of several hours. In a preferred variant of the method, this decomposition is suppressed by carrying out the in situ preparation of the CuH (e.g. from CuCl) in the presence of one equivalent of triphenylphosphine based on CuH, or alternatively employing preformed Stryker's reagent as precatalyst. The CuH-$PPh_3$ complex which is then initially present is thermally stable in the range from −20° C. to 0° C., but causes no significant reduction of keto groups under these conditions. Only when this "CuH storage form" encounters the few chiral diphosphane molecules in the reaction mixture is the chiral, highly reactive CuH complex produced by transcomplexation and reduces, in a ligand-promoted reaction, the keto groups to optically active alcohols.

It is possible, depending on the silane employed, on the reaction conditions and the work up conditions, for the asymmetric hydrosilylation of the ketone to be managed so that the isolated reaction product is either directly the free, optically active alcohol or else its silyl ether which can then optionally be deprotected to the free alcohol, or else can be reacted further in the protected form. Use of PMHS and direct isolation of the free, optically active alcohol frequently gives better results and is therefore preferred. The use of other silanes, e.g. TBS-H or TES-H, followed by isolation of the tert-butyldimethylsilyl ether or of the triethylsilyl ether of the chiral alcohol, is, however, likewise one of the embodiments of the present invention.

The resulting hydroxy group can then optionally be protected ($R^{10}$=H atom or protective group, the latter for example Ac, Si(alkyl)$_o$(aryl)$_p$ with o, p=0, 1, 2 or 3 and o+p=3). Preference is given in this connection to silyl protective groups, the trityl, the THP, the 1-ethoxyethyl and the alkoxymethyl protective groups, and the tert-butyldimethylsilyl group, the trityl, the THP and the ethoxymethyl groups are particularly preferred. Introduction of the protective groups takes place by methods known to the skilled worker as described for example in "Protective Groups in Organic Synthesis" Third Edition [T. W. Green, P. G. M. Wuts (editors), John Wiley & Sons, Inc., 1999].

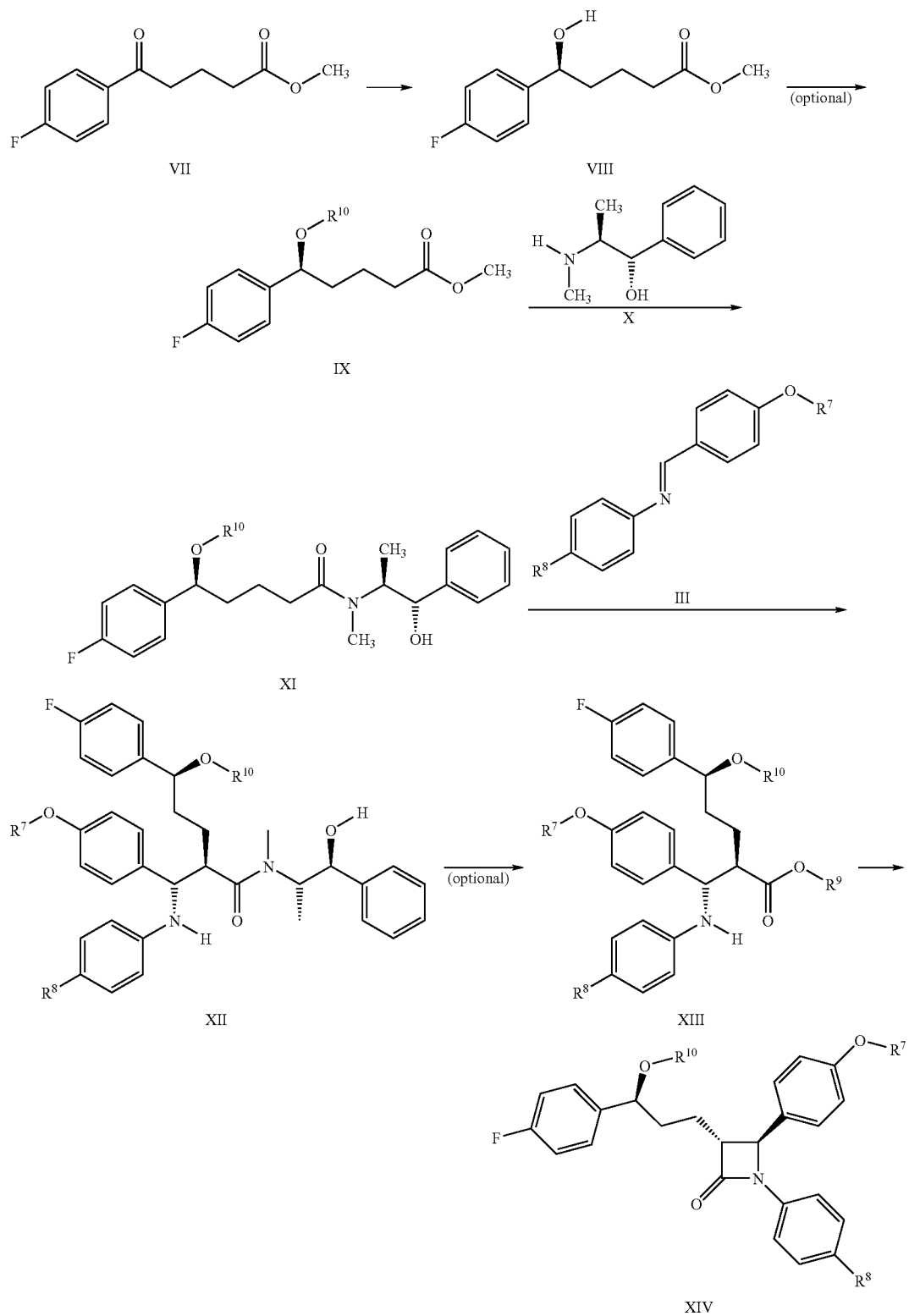

The ester (IX) is then converted with (+)-(1S,2S)-pseudoephedrin (X) into the amide (XI). All methods known to the skilled worker can be employed in this case. Examples thereof are described by A. G. Myers et al described in J. Am. Chem. Soc. (1997, Volume 119, pages 6496-6511, 656-673) and in Organic Synthesis (1999, Volume 76, pages 57 to 76).

A reliable and mild, but multistage method for converting the ester (IX) into the amide (XI) consists of initially hydrolyzing the methyl ester to the free carboxylic acid, then reacting the latter with about 1.0 equivalents of a suitable carbonyl chloride, e.g. pivaloyl chloride, or of a chloroformic ester, e.g. isobutyl chloroformate, in the presence of a suitable base, preferably approx. 2.2 equivalents of the base triethylamine, in a suitable solvent, preferably dichloromethane, acetone or toluene, at about 0° C., to give the mixed anhydride, which then reacts, preferably in a one-pot reaction at about 0° C., on addition of about 1.0 equivalent of (+)-(1S,2S)-pseudoephedrine (X) to give the amide (XI).

An additional possibility is also to obtain the amide (XI) in one stage by direct condensation of ephedrine with the methyl ester (IX) under basic conditions in accordance with one of the following two variants. In the first variant, (+)-(1S,2S)-pseudoephedrine [1.0 to 1.2 equivalents based on the ester (IX)] is deprotonated in a suitable solvent, preferably from the class of ethers, particularly preferably in THF, in the presence of anhydrous lithium chloride (approx. 2 equivalents), with n-butyllithium solution (2.5 to 10 M in hexanes, 0.1 to 1.0 equivalent based on pseudoephedrine, preferably 0.2 to 0.6 equivalent, particularly preferably 0.25 to 0.4 equivalent) in the temperature range from −78 to +20° C., preferably at −20° C. to +10° C., particularly preferably at −5° C. to +5° C. A solution of 1.0 equivalent of the methyl ester (IX), preferably in the same solvent, is then added dropwise, and the reaction mixture is left to stir further in the temperature range from −20° C. to +40° C., preferably at 0° C. to +25° C., particularly preferably at +15° C. to +25° C. It is assumed that this one-stage synthesis of the pseudoephedrine amide (XI) involves an original transesterification reaction of the methyl ester with the secondary hydroxy group of pseudoephedrine, followed by an intramolecular O→N acyl shift.

In an alternative second variant, substoichiometric amounts of sodium methanolate or lithium methanolate are employed instead of n-butyllithium for deprotonating the pseudoephedrine. From 0.2 to 0.6 equivalent of NaOMe or LiOMe, based on pseudoephedrine, are preferably used, particularly preferably 0.4 to 0.5 equivalent. The other reaction parameters correspond to the first variant described above. The first and the second variant ordinarily afford comparable yields of amide (XI).

The imine building block (III) which is necessary for the subsequent addition is obtained by known methods from the corresponding aniline derivative and aldehyde. The water produced in the reaction in this case can be removed for example by azeotropic distillation with toluene.

The enolate is prepared from the amide (XI) with the appropriate bases and undergoes addition onto the imine (III). This results in Mannich products (XII). General examples thereof are described in J. Org. Chem. (2001, Volume 66, page 9030-9032), Organic Letters (2001, Volume 3, page 773-776 and 2000, Volume 2, page 3527-3529). Conversion of the amide (XI) into the Mannich product (XII) is a one-pot reaction which proceeds through 2 to 4 phases which are described below. All the phases of the reaction are carried out in a rather polar solvent having ether properties, which must have good solubility properties for lithium salts and good stability towards lithium bases. Preferred solvents are tetrahydrofuran, 1,4-dioxane, 1,2-dimethoxyethane, diethoxymethane (DEM, formaldehyde diethylacetal), 1,1-dimethoxymethane (methylal), diglyme (diethylene glycol dimethyl ether), triglyme (triethylene glycol dimethyl ether) and dichloromethane. Tetrahydrofuran and diethoxymethane are particularly preferred, especially tetrahydrofuran. Addition of the enolate of amide (XI) as imine (III) takes place at the desired reaction temperature of from −10° C. to +40° C. at an adequate speed and substantially completely only if the reaction medium is substantially saturated with an anhydrous lithium salt, preferably lithium chloride. This state is achieved with the particularly preferred solvents in the stated temperature range when the reaction mixture comprises about 3 to 8 equivalents of the lithium salt based on the amide (XI), preferably 4 to 6.5 equivalents. It is not critical whether the lithium salt is introduced into the reaction mixture only for the enolate addition onto the imine (stage 4), or whether it is added earlier so that it is present even during phases 1, 2 or 3.

Phase 1 [obtaining the lithium base]: suitable bases are lithium diisopropylamide (LDA) or 1,1,1,3,3,3-hexamethyldisilazane lithium salt (LiHMDS, lithium bistrimethylsilylamide). LDA is preferred. It is possible either to employ the commercially available bases, or the lithium bases obtainable in situ by addition of a bare equivalent of n-BuLi solution to the solution of diisopropylamine or 1,1,1,3,3,3-hexamethyldisilazane (HMDS, bistrimethylsilylamine) are used. For the in situ generation of the lithium base, the solution of the amine in one of the abovementioned dry solvents having ether properties, particularly preferably THF, is introduced into a thoroughly dried reaction vessel under an inert gas. It is optionally possible for the lithium salt required in phase 4, preferably lithium chloride, to be already dissolved/partially suspended in this solution. From 0.92 to 0.99 equivalent, based on the amine, of a 1.5 to 10.0 molar solution of n-butyllithium in hexane, preferably about 0.95 equivalent of an approx. 2.5 molar solution, are slowly added at from −78° C. to +10° C., preferably at −30° C. to 0° C., particularly preferably at −20° C. The mixture is allowed to warm to 0° C. and is then stirred at this temperature for 5 to 10 min.

Phase 2 [conversion of the amide (XI) into the lithium enolate]: deprotonation of the pseudoephedrine amide (XI) to the lithium enolate is carried out with 2.0 to 3.2 equivalents of the lithium base, preferably with about 2.05 equivalents of LDA, as long as the amide (XI) contains no further unprotected protic function (OH, NHR) apart from the hydroxy group of the pseudoephedrine. Otherwise, it is necessary additionally to employ the amount of lithium base necessary to deprotonate this function. The lithium salt required in phase 4, preferably lithium chloride, can optionally already be dissolved/partially suspended in the reaction mixture. Deprotonation of the amide (XI) to the lithium enolate with LDA is carried out at from −78° C. to +40° C., preferably at −20° C. to +20° C. The solution of the amide (XI) is particularly preferably added dropwise at about −20° C., over the course of about 30 min-1 h, to the solution of LDA solution which may optionally additionally comprise lithium chloride. The mixture is stirred at −20° C. for about 15 to 30 min, allowed to warm to 0° C. over the course of about 30 min and is then stirred at this temperature for 15 min. The enolization is normally rapid at 0° C. and therefore complete at this time. However, it is then optionally possible to warm quickly to +25° C. and stir at this temperature for a further 5 min, because pseudoephedrine amide enolates have good thermal stability (half-life>12 h; see A. G. Myers et al, J. Am. Chem. Soc. 1997, 119, 6496, page 6497 therein). Deprotonation of the amide (XI) to the lithium enolate with LiHMDS, preferably 3.0 to 3.5 equivalents, is carried out at −78° C. to +40° C., preferably at −20° C. to +20° C. The solution of LiHMDS, preferably about 3.2 equivalents, is particularly preferably slowly added dropwise at −5° C. to 0° C. over the course of about 30 min to the solution of the amide (XI), which may optionally comprise about 4 equivalents of lithium chloride. This is followed by stirring at 0° C. for a further hour.

Phase 3 [optionally transmetallation of the amide lithium enolate]: the lithium enolate of the pseudoephedrine amide (XI) may be transmetallized to the titanium enolate boron enolate, zinc enolate before the Mannich addition onto the imine (III), or alternatively be employed directly without previous transmetallation for the Mannich addition (phase 4). Direct use of the lithium enolate or transmetallation to the zinc enolate are preferred, and the use of the lithium enolate without transmetallation is particularly preferred. The zinc enolate is generated by cooling the solution of the lithium enolate obtained in phase 2 and adding at −78° C. to 0° C., preferably at −20° C. to 0° C., the solution of 2 equivalents of anhydrous zinc chloride in THF. If addition of the $ZnCl_2$ took place at −78° C., the mixture is subsequently stirred at this temperature for 1 hour. If the addition took place at −20° C. to 0° C., the subsequent stirring time is only 30 to 10 minutes.

Phase 4 [Mannich addition of the amide enolate onto the imine (III)]: the enolate of pseudoephedrine amide (XI) generated in phase 2 or phase 3 undergoes addition onto the imine (III) to form the 2,3-anti-3-arylamino carboxamide (XII) with high anti/syn—and π side diastereoselectivity. The ratio of the desired diastereomers (XII) to the total of all the other diastereomers was >85% de in the examples investigated, and in some cases up to 97% de. The addition is carried out in the presence of from 3 to 8 equivalents of lithium salt, preferably lithium chloride, particularly preferably in the presence of from 4 to 6.5 equivalents of lithium chloride. From 1.1 to 5.0 equivalents of the imine (III), based on the amide enolate, are employed, preferably 1.3 to 4.0 equivalents, particularly preferably 1.5 to 2.0 equivalents. The Mannich addition is carried out at from −20° C. to +30° C., preferably at −10° C. to +20° C., particularly preferably at 0° C. to +10° C. In a particularly preferred embodiment, from 1.5 to 2.0 equivalents of a 1 molar solution of the imine (III) in THF are added dropwise at 0 to +10° C. over the course of 10 min to 1 equivalent of a 0.2 to 0.5 molar solution of the lithium enolate in THF, which comprises 6 to 6.5 equivalents of lithium chloride, and then the mixture is stirred at this temperature for 1 to 3 hours. The reaction mixture is worked up, and the Mannich product (XII) is isolated by the usual methods which are well known to the skilled worker.

Elimination of pseudoephedrine can take place by acid hydrolysis with protic acids or with Lewis acid. However, pseudoephedrine amides can also be cleaved by basic hydrolysis or in boiling water. Examples thereof are to be found in the aforementioned publications by A. G. Myers, and in D. Badia et al, J. Org. Chem. 2001, 66, 9030-9032 and Org. Lett. 2001, 3 (5), 773-776. Basic hydrolysis is preferred for amide cleavage of the α-alkyl-substituted β-aryl-β-arylaminopropionic acid pseudoephedrine amides (XII) of the present invention, because impurities may be produced under acidic conditions, because of elimination reactions, and because the amide cleavage proceeds only very slowly in boiling water. During the basic amide cleavage in boiling, aqueous ethanolic sodium hydroxide solution there may be epimerization to a greater or lesser extent of the α position, which must be curbed as far as possible. It has been found that the rate of the basic amide hydrolysis and the extent of the α-epimerization occurring during it depend to a great extent on whether and how the 5(S)-hydroxy group in the Mannich product (XII) is protected. With reaction parameters which are otherwise identical, the rate of basic amide hydrolysis is a maximum and the α-epimerization is a minimum when the Mannich product (XII) with unprotected 5(S)-hydroxy group is employed (i.e. $R^{10}$=H). If (XII) having a protective group which is not inert towards the highly basic reaction conditions is employed, the rate of amide cleavage is greater and the α-epimerization is less when the protective group $R^{10}$ is eliminated more quickly. If an inert protective group $R^{10}$ is used, the amide hydrolysis is slow and the extent of α-epimerization is high, this being more the case as the nonpolarity of the inert protective group $R^{10}$ increases. The basic amide cleavage employing the Mannich product (XII) with unprotected 5(S)-hydroxy group ($R^{10}$=H) is therefore preferred. An alternative possibility is also to eliminate the pseudoephedrine by using an amide-cleaving enzyme. A further alternative is amide cleavage with palladium (II) perchlorate tetrahydrate in 0.1 M phosphate buffer solution at pH 7.0 and 25° C., as described by N. M. Kostic et al, J. Am. Chem. Soc. 2004, 126, 696-697.

The protective groups can, if desired, optionally be reintroduced into the product of the amide-cleavage reaction (formula XIII) by methods known to the skilled worker [see "Protective Groups in Organic Synthesis" (T. W. Green, P. G. M. Wuts (editors), John Wiley & Sons, Inc., 1999)].

The carboxylic acid (XIII) with $R^9$=H which can be obtained thus in the optional variant can be converted into the β-lactam (XIV) directly or after activation—in which case $R^9$ is $(C_1-C_4)$alkyl, $CO(C_1-C_4)$alkyl, $COO(C_1-C_4)$alkyl, $SO_2$-aryl. This is also possible directly from (XII). A review of the possible reaction conditions is to be found in "Methoden der Organische Chemie (Houben-Weyl)" (Volume 16b, pages 60 to 114, Georg Thieme Verlag Stuttgart, New York, 1991). The carboxylic acid (XIII, $R^9$=H) is preferably converted into the methyl ester (XIII, $R^9$=$CH_3$), and the latter is cyclized in the presence of a base to the β-lactam (XIV). This cyclization is particularly preferably carried out with 1 to 2 equivalents of lithium bis(trimethylsilyl)amide (LHMDS) as base into THF as solvent. The cyclization is carried out in the temperature range from −40° C. to +50° C., preferably at −20° C. to +25° C., particularly preferably at −10° C. to 0° C.

The protective groups can finally be eliminated by methods known to the skilled worker.

Where the compounds of the formula (VI) are to be reacted further to give compounds of the formula (I) in which $R^2$ is $CH_2NHR^4$ ($R^4$≠H), amines of the formula (VI), i.e. compounds in which $R^8$ after the deprotection is $R^2$ and specifically $CH_2NHR^4$ with $R^4$=H, are reacted with compounds of the formulae (XV) or (XVI)

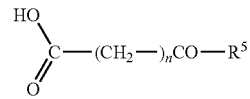

(XV)

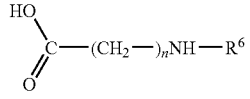

(XVI)

to give the desired compounds (I) after previous protective group elimination (via peptide coupling). Other compounds of the formula (I) are produced by simple deprotection of the corresponding compounds of the formula (VI) without further reactions.

The terms used in definitions moreover have the following meanings (unless already specified above):

Ac=acetyl; alkyl=$(C_1-C_{14})$alkyl, preferably $(C_1-C_8)$alkyl, unbranched or branched; aryl=$(C_6-C_{10})$aryl; p in front of a substituent such as "pOCH$_3$" means position 4 on the aromatic system.

The process of the invention ensures that the diphenylazetidinone derivatives which are known per se can be prepared in good yield and without the disadvantages of the prior art, such as the use of auxiliary reagents which lead to unwanted by-products.

The following examples are provided to more specifically describe how one skilled in the art may practice the inventive process of the present invention and produce the claimed compositions defined herein. It is to be recognized that they are for illustrative purposes only and should not be construed as limiting the true spirit of and scope of the invention as recited by the claims that follow.

Examples 1 to 14 and 18 to 35 show the preparation of precursors or intermediates, and Examples 15 to 17 show the generation of diphenyl-azetidinones and the deprotection thereof. A reference example C1 is additionally indicated for comparative purposes.

EXAMPLE 1

Methyl 5-(4-fluorophenyl)-5(S)-hydroxypentanoate By Asymmetric (R)-Me-CBS—Catalyzed Keto Reduction

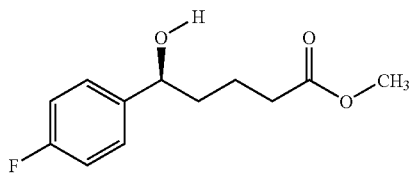

890 ml of dichloromethane are introduced under nitrogen into a four-neck round-bottom flask with mechanical stirrer, dropping funnel with micrometering and thermosensor. 210 ml (420 mmol) of a 2 M solution of borane-dimethyl sulfide complex in THF are added, and the solution is then cooled to −5° C. 21 ml (21.4 mmol) of a 1.02 M solution of (R)-tetrahydro-1-methyl-3,3-diphenyl-1H,3H)-pyrrolo[1,2-C][1,3,2]oxazaborolidine in toluene ["(R)-Me CBS", supplied by Strem] are added, and the reaction mixture is stirred at −5° C. for 15 min. A solution of 93.5 g (414.5 mmol) of 99.4% pure methyl 5-(4-fluorophenyl)-5-oxo-pentanoate in 600 ml of dichloromethane is added dropwise at a uniform rate over the course of 3 h at −5° C., followed by stirring for 1 h. A check by thin-layer chromatography (=TLC) (ethyl acetate/n-heptane 8:2) shows complete conversion of the keto ester to the hydroxy ester. 60 ml (approx. 1470 mmol) of methanol are added dropwise over the course of 30 min, followed by slow dropwise addition of 255 ml (approx. 2960 mmol) of 35% strength aqueous hydrogen peroxide. This dropwise addition is accompanied by evolution of much heat and evolution of gas. 83 ml of 2-normal aqueous sulfuric acid are added dropwise, and the mixture is stirred for 15 min. The organic phase is separated off and washed successively with 600 ml of 2-normal aqueous sulfuric acid, 3×600 ml of 5% strength aqueous sodium sulfite solution and 600 ml of saturated aqueous sodium chloride solution. The solution is dried, filtered, concentrated in vacuo, and the residue is dried under high vacuum (=HV). 91.6 g (405 mmol according to weight) of yellowish oil are obtained. HPLC (100 area % analysis, 250× 4.6 mm Chiralpak AD-H; 15° C.; n-hexane/EtOH 90:10; 1 ml/min.; det. 210 nm) indicates 92% chemical purity and 96% ee (ee is the abbreviation for enantiomeric excess) [$t_{ret}$ of (S)-enantiomer: 13.8 min., (R)-enantiomer: 16.7 min.]. The yield corrected for the chemical purity is thus 90% of theory.

$^1$H-NMR (400 MHz, CDCl$_3$): δ=1.55-1.85 (m, 4H, 2×CH$_2$), 2.03 (s, broad, 1H, OH), 2.34 (td, 2H, CH$_2$CO$_2$), 3.66 (s, 3H, OCH$_3$), 4.67 (t, 1H, C$\underline{H}$—OH), 7.03 (~t, 2H, arom.-H), 7.31 (~dd, 2H, arom.-H).

EXAMPLE 2

Methyl 5(S)-(tert-butyldimethylsilanyloxy)-5-(4-fluorophenyl)pentanoate

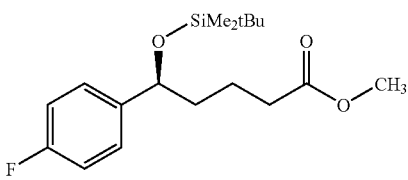

A solution of 90.5 g (368 mmol) of the 92% pure hydroxy ester from Example 1 in 800 ml of dichloromethane is introduced into a 2-neck round-bottom flask with mechanical stirrer, dropping funnel and thermosensor under nitrogen. 54.5 g (800 mmol) of imidazole are added and dissolved after brief stirring, during which the internal temperature falls from 20° C. to 13° C. A solution of 74.5 g (479 mmol) of 97% pure tert-butyldimethyl-chlorosilane in 135 ml of dichloromethane is added dropwise, during which the internal temperature rises from 14° C. to 27° C. and a white precipitate separates out. The reaction mixture is then boiled under reflux for 4 h. A TLC check (ethyl acetate/n-heptane 1:1) now shows only a trace of precursor. The suspension is filtered through 200 g of silica gel 60 (Merck, 0.035-0.07 mm) which have been packed into a column as slurry in 500 ml of dichloromethane. Washing (elution) is carried out with 2×250 ml of ethyl acetate. The combined organic phases are concentrated in vacuo, and the residue is dried under HV. 136.5 g (400 mmol according to weight) of pale yellow oil are obtained. HPLC (250×4.6 mm Chiralpak AD-H; 10° C.; n-hexane/iPrOH 95:5; 0.5 ml/min.; det. 210 nm) indicates 96% ee [$t_{ret}$ of (R)-enantiomer: 5.7 min., (S)-enantiomer: 6.6 min.].

$^1$H-NMR (400 MHz, CDCl$_3$): δ=−0.15 (s, 3H, Si—CH$_3$), 0.02 (s, 3H, Si—CH$_3$), 0.88 (s, 9H, Si-tBu), 1.55-1.75 (m, 4H, 2×CH$_2$), 2.28 (td, 2H, CH$_2$—CO$_2$), 3.65 (s, 3H, OCH$_3$), 4.65 (~t, 1H, C$\underline{H}$—OSi), 6.98 (~t, 2H, arom.-H), 7.24 (~dd, 2H, arom.-H).

EXAMPLE 3

[2(S)-Hydroxy-1(S)-methyl-2-phenylethyl]-N-methyl-5(S)-(tert-butyldimethyl-silanyloxy)-5-(4-fluorophenyl)pentanamide

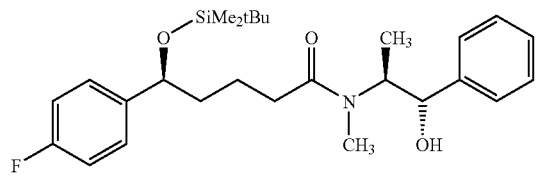

A solution of 5.03 g (117 mmol) of anhydrous 99% pure lithium chloride and 9.9 g (58.7 mmol) of 98% pure (+)-(1S, 2S)-pseudoephedrine in 81 ml of absolute THF in a thoroughly heat-dried three-neck round-bottom flask with magnetic stirrer, septum and thermometer is cooled to <2° C. in an ice bath. 5.9 ml (14.6 mmol) of a 2.5 molar solution of n-butyllithium in hexane are added dropwise by syringe through the septum over the course of 10 min, during which the internal temperature of the clear reaction solution rises to 5° C. After 10 min, a solution of 25 g (53.6 mmol) of the 73% pure ester from Example 2 in 17 ml of absolute THF is added dropwise over the course of 30 min. The reaction mixture is then stirred at room temperature for 36 h. A TLC check (ethyl acetate/n-heptane 1:1) shows the precursor and the product in the ratio of about 1:3. 80 ml of water are added dropwise, initially slowly and then more quickly, to the reaction mixture cooled in ice, during which two phases form. Most of the THF is distilled off in vacuo (90 ml of distillate). The aqueous residue is extracted firstly with 80 ml of dichloromethane and then again with 2×40 ml of dichloromethane. The combined extracts are dried over potassium carbonate, filtered, concentrated in vacuo, and the residue is dried under HV. 34.6 g of viscous yellow oil are obtained. Column chromatography of the crude product (900 g of Merck silica gel 60, 0.04-0.063, elution with 3 l of dichloromethane, followed by dichloromethane/methanol (2l of 99:1, then 2 l of 98:2, then 4 l of 97:3; flow rate 80 ml/min; 250 ml fractions) affords 5.4 g (13.5 mmol, 25% of theory) of approximately 85% pure recovered ester (fractions 6-9) and 19.0 g (40.1 mmol, 75% of theory) of the amide (fractions 33-41). Reaction of the recovered ester in analogy to the above method but with use of 0.4 equivalent (instead of 0.25 equivalent) of n-BuLi based on (+)-pseudoephedrine leads to complete conversion of the ester and affords, after extraction with ethyl acetate (instead of dichloromethane), a further 4.4 g (9.3 mmol) of the amide. The overall yield (pale yellow resin) thus amounts to 23.4 g (49.4 mmol, 92% of theory).

HPLC [column: 250×4.6 mm (R,R)-Whelk 01; eluent: n-hexane/iPrOH 90:10; flow rate: 1 ml/min.; temp.: 25° C.; Det.: 210 nm, $t_{ret}$ of 5(S)-silanyloxy diastereomer 8.4 min.; peak of the same UV spectrum (probably 5(R)-diastereomer): $t_{ret}$ 7.4 min.] indicates a diastereomer purity of 96% de (de is abbreviation for diastereomeric excess). $^1$H-NMR (400 MHz, $CDCl_3$): two sets of signals owing to the presence of two rotamers (ratio about 2.8:1) of the amide function. Signals of the main rotamer are identified by (*), and signals of the subsidiary rotamer by ( ). Unidentified signals are ascribed to overlapping rotamer signals. δ=−0.12 (s, 3H, Si—$CH_3$), 0.03 (s, 3H, Si—$CH_3$), 0.89 (s, 9H, Si-tBu), 0.92 (#, d, 3H, CH—$CH_3$), 1.09 (*, d, 3H, CH—$CH_3$), 1.5-1.8 (m, 4H, 2×$CH_2$), 2.20-2.48 (m, 2H, $CH_2$CON), 2.78 (*, s, 3H, N—$CH_3$), 2.89 (#, s, 3H, N—$CH_3$), 3.93 (#. qui, 1H, C$\underline{H}$$CH_3$), 4.20 (s, broad, 1H, OH), 4.42 (*, qui, 1H, C$\underline{H}$$CH_3$), 4.57 (m, 1H, C$\underline{H}$OH), 4.67 (m, 1H, C$\underline{H}$OSi), 6.97 (~t, 2H, arom.-H), 7.20-7.40 (m, 7H, arom.-H).

HPLC-MS (TOF, positive ESI) [TOF is the abbreviation for a time of flight mass spectrometer; ESI is the abbreviation for electrospray ionization): m/z=474 (100%, M+H$^+$), 342 (64%, M+H$^+$-tBuMe$_2$SiOH).

EXAMPLE 4

(4-Methoxybenzylidene)-(4-{[(4-methoxybenzylidene)amino]methyl}-phenyl)amine

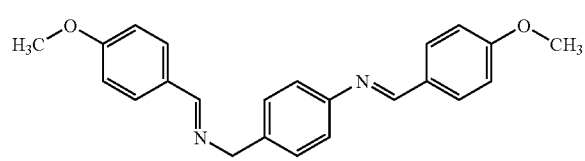

430 ml of toluene and 40 ml (349 mmol) of 99% pure 4-aminobenzylamine are introduced into a four-neck flask with mechanical paddle stirrer, water trap and reflux condenser. A two-phase mixture is obtained owing to the low solubility of the amine. 96 ml (775 mmol) of 98% pure anisaldehyde are added, and the mixture is heated with an oil bath heated to 140° C. In the heating-up phase, the reaction mixture starts to boil at around 80° C., and cloudy water/toluene azeotrope distills into the water trap. After about 30 min, the maximum internal temperature is 114° C., and only clear toluene now distills over. 12.5 ml of water (corresponding to about 100% of theory of the two equivalents of water) separate out. A TLC check (plate deactivated by previously standing in NEt$_3$(triethylamine) vapor-saturated tank, ethyl acetate/n-heptane 1:1 plus 1% NEt$_3$) indicates complete conversion of the 4-aminobenzylamine. The mixture is actively cooled to room temperature. A mixture of 800 ml of n-heptane and 200 ml of ethyl acetate is then run slowly in, during which, after addition of only about 200 ml, a pale yellow precipitate separates out spontaneously. The mixture is stirred for 1 h, and the precipitate is filtered off with suction and dried under HV. Yield: 105.6 g.

The filtrate is concentrated to about 50 ml in vacuo. A mixture of 160 ml of heptane and 40 ml of ethyl acetate is added dropwise to the remaining suspension. After stirring for 30 minutes, the precipitate is filtered off with suction and dried under HV. Yield: 15.6 g.

Overall yield: 121.2 g (338.1 mmol, 97% of theory) of yellow crystals.

$^1$H-NMR (400 MHz, CDCl$_3$): δ=3.84 (s, 3H, OCH$_3$), 3.88 (s, 3H, OCH$_3$), 4.80 (s, 2H, CH$_2$), 6.93 (d, 2H, arom.-H), 6.98 (d, 2H, arom.-H), 7.18 (d, 2H, arom.-H), 7.34 (d, 2H, arom.-H), 7.73 (~d, 2H, arom.-H), 7.84 (~d, 2H, arom.-H), 8.32 (s, 1H, N═CH), 8.39 (s, 1H, N═CH).

EXAMPLE 5

[2(S)-Hydroxy-1(S)-methyl-2-phenylethyl]-N-methyl-5(S)-(tert-butyldimethyl-silanyloxy)-5-(4-fluorophenyl)-2(R)-[(4-{[(4-methoxybenzylidene)amino]-methyl}phenylamino)-(4-methoxyphenyl)-(S)-methyl]pentanamide ("Imine-protected Mannich product")

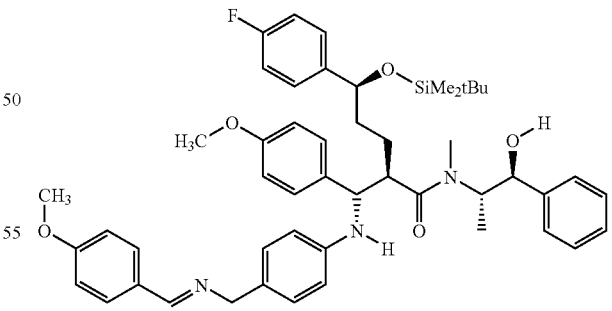

Lithium chloride (99% pure) is dried at 150-200° C./4× 10$^{-3}$ mbar for 3 h. Diisopropylamine (99.5% pure) is freshly distilled from CaH$_2$ and then contains 0.02% by weight water according to Karl-Fischer titration. Tetrahydrofuran (THF) is degassed by bubbling through dried argon, and contains <0.005% by weight of water according to Karl-Fischer titration. 47.6 ml of THF and 12.6 ml (89.6 mmol) of diisopropylamine are added to 10.1 g (236 mmol) of dried lithium chloride in a thoroughly heat-dried three-neck round-bottom flask with magnetic stirrer, septum, dropping funnel with nitrogen inlet tube and low-temperature thermometer. The mixture is cooled to −78° C. in dry ice/acetone bath, and 33.2 ml (82.7 mmol) of a 2.5 molar solution of n-butyllithium in hexane are added dropwise by syringe pump over the course of 20 min. The reaction mixture is allowed to warm to 0° C., becoming very cloudy at −30° C., and is stirred at 0° C. for 5 min. It is again cooled to −78° C., resulting in a thick slurry which can be stirred only with difficulty. A solution of 18.9 g (40.0 mmol) of the pseudoephedrine amide (from Example 3) in 80 ml of THF is added dropwise through the dropping funnel over the course of 30 min. To improve the stirring effect of the magnetic stirrer, the cooling bath is initially removed briefly, during which the internal temperature rises to a maximum of −50° C. The mixture quickly becomes less viscous, so that the reaction flask can be reimmersed in the cooling bath. Stirring is continued at −78° C. for 1 h. The mixture is allowed to warm to 0° C., is stirred at this temperature for 15 min and at room temperature for a further 5 min, and is cooled again to 0° C. A solution of 28.6 g (79.7 mmol, 2 equivalents based on amide) of the bisimine (from Example 4) in 95 ml of THF is added dropwise over the course of 20 min, during which the reaction mixture becomes dark in color. It is then stirred at 0° C. for 1 h.

HPLC check [column: 150×4.6 mm Zorbax Eclipse XDB-C8; mobile phase: eluent A (NEt$_3$/AcOH—buffer 20 mM pH 7.0), eluent B (CH$_3$CN); gradient A:B from 9:1 within 15 min linear to 1:9, then 10 min isocratic A:B=1:9; temp. 25° C., flow rate 1 ml/min.; det. 254 nm (210 nm for amide and for pseudoephedrine); conc. of the sample solution about 2 mg/ml; volume injected 5 µl ] shows substantial conversion of the pseudoephedrine amide ($t_{ret}$ 17.4 min.) to the Mannich product ($t_{ret}$ 19.5 min.) and small amounts of its diastereomer ($t_{ret}$ 18.8 min.). The imine-deprotected Mannich product is indicated in a small amount as broadened peak ($t_{ret}$ 16.9 min.) and derives from hydrolysis in the HPLC injection solution. Excess bisimine is indicated at $t_{ret}$ 13.9 min, its hydrolysis product anisaldehyde at $t_{ret}$ 9.1 min and traces of pseudoephedrine at $t_{ret}$ 4.0 min. The reaction mixture is poured under nitrogen into a mixture of 1.6 l of 10% strength aqueous acetic acid and 1.6 l of dichloromethane which is vigorously stirred mechanically and cooled to 0° C. in a 4 l flask, the color becoming paler and yellow. The mixture is allowed to warm to room temperature, the organic phase is separated off, and the aqueous phase (pH 3-4) is extracted with 2×600 ml of dichloromethane. The combined organic phases are washed with a total of 1.4 l of saturated aqueous NaHCO$_3$ solution, with washing solution being replenished until the pH of the aqueous phase after shaking stays at pH 7-8. The organic phase is dried over potassium carbonate, filtered, concentrated in vacuo, and the residue is dried under HV. 41.7 g of crude product are obtained as a viscous brown resin. The contents are determined by HPLC. For this purpose, chromatographically purified samples of the imine-protected Mannich product and of the imine-deprotected Mannich product are used as reference standards. Calibration solutions (0.2-0.8 mg/ml) are prepared by accurately weighing the two standards into three volumetric flasks in each case. The HPLC peak area produced by each of these calibration solutions for the imine-protected Mannich product or the imine-deprotected Mannich product is plotted against the respective concentration of the calibration solutions, and two calibration lines are obtained in this way. Subsequently, three samples of the crude product are accurately weighed into volumetric flasks. The contents of the imine-protected Mannich product and of the imine-deprotected Mannich product can be read off the calibration lines using the HPLC peak areas produced by these samples. The crude product accordingly contains 57% by weight of imine-protected Mannich product and 8% by weight of imine-deprotected Mannich product.

This corresponds to a yield of 23.8 g (28.6 mmol, 71.4% of theory) of protected Mannich product and 3.3 g (4.6 mmol, 11.6% of theory) of imine-deprotected Mannich product. The overall yield of Mannich product amounts to 33.2 mmol (83% of theory).

Purified imine-protected Mannich product is obtained by preparative HPLC [100×19 mm (BV=28.3 ml) Xterra C18 MS 5 µm (Waters); eluent A (20 mM triethylamine in water with acetic acid to pH 7), eluent B (acetonitrile/water 95:5); gradient and flow rate: 25 min. isocratic 10 ml/min. 30% A/70% B, then linear within 45 min at 9 ml/min. to 0% A/100% B; linear flow rate 193 cm/h; column temp. 19-22° C.; det. 254 nm; solution for loading: 100 mg of crude product are dissolved in 6.5 ml of eluent B and diluted with 3 ml of eluent A, and the resulting solution is loaded; product isolation: the pure fraction is run into 30 ml of magnetically stirred chloroform, and the chloroform phase is separated off using a separating funnel and evaporated to dryness in vacuo at 25° C.].

$^1$H-NMR (400 MHz, CDCl$_3$): two sets of signals owing to the presence of two rotamers (ratio about 3.5:1) of the amide function. Signals of the main rotamer are identified by (*), and signals of the subsidiary rotamer by (#). Unidentified signals are ascribed to overlapping rotamer signals. δ=−0.23 (#, s, 3H, Si—CH$_3$), −0.15 (*, s, 3H, Si—CH$_3$), −0.11 (#, s, 3H, Si—CH$_3$), −0.02 (*, s, 3H, Si—CH$_3$), 0.69 (*, d, 3H, CH CH$_3$), 0.75 (#, s, 9H, Si-tBu), 0.79 (#, d, 3H, CHCH$_3$), 0.86 (*, s, 9H, Si-tBu), 1.40-2.10 (m, 5H, 2×CH$_2$, CHC$\overline{ON}$), 2.32 (*, s, 3H, NCH$_3$), 2.88 (#, s, 3H, NCH$_3$), 3.08 (*, m, 1H, NH—CH), 3.24 (#, m, 1H, NH—CH), 3.75 (*, s, 3H, OCH$_3$), 3.78 (#, s, 3H, OCH$_3$), 3.87 (s, 3H, OCH$_3$), 4.12 and 4.38-4.80 (m, 6H, CHCH$_3$, CH—OH, CH—OSi, =N—CH$_2$), 6.45 (*, d, 2H, arom.-H), 6.50 (#, d, 2H, arom.-H), 6.78 (d, 2H, arom.-H), 6.80-7.08 (m, 6H, arom.-H), 7.08-7.47 (m, 9H, arom.-H), 7.70 (~d, 2H, arom.-H), 8.22 (#, s, 1H, CH=N), 8.26 (*, s, 1H, CH=N).

HPLC-MS (infusion, TOF, positive ESI): m/z=854 (7%, M+Na$^+$), 832 (2%, M+H$^+$), 697 (100%, M+Na$^+$-tBu).

EXAMPLE 6

[2(S)-Hydroxy-1(S)-methyl-2-phenylethyl]-N-methyl-2(R)-[(4-aminomethyl-phenylamino)-(4-methoxyphenyl)-(S)-methyl]-5(S)-(tert-butyldimethyl-silanyloxy)-5-(4-fluorophenyl)pentanamide] ("Imine-deprotected Mannich Product")

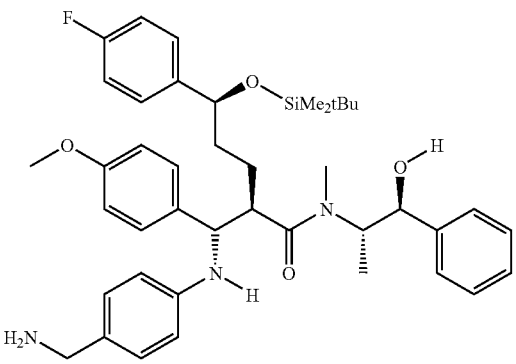

A clear solution of 450 mg of the crude Mannich product from Example 5 is prepared in 1.0 ml of acetonitrile. 0.4 ml of deionized water is added, whereupon the brown solution becomes slightly cloudy. 45 µl (0.78 mmol) of glacial acetic acid are added dropwise by syringe, followed by a further 0.6 ml of deionized water. The resulting solution has a pH of 5.4. Analytical HPLC of the solution after standing at room temperature for 1 hour indicates almost complete conversion. The solution is injected onto a semipreparative HPLC column [19×100 mm Xterra C18 MS, 5 μm (Waters)] and eluted with the following gradient [solvent A: 20 mM NEt$_3$ in water, pH 7 with acetic acid; solvent B: CH$_3$CN/water 95:5 v/v; A:B=60:40 (10 ml/min.) within 28.5 min linear to A:B=27:73 (10 ml/min.); then 3.9 min isocratic A:B=27:73 (9 ml/min.); then for washing within 0.1 min to 100% B (9 ml/min.), 7 min isocratic with 100% B (9 ml/min.) and then back to A:B=60:40]. The pure product eluate fraction (t$_{ret}$=23-25 min.) is collected, concentrated at 100 mbar and 30° C., and then extracted three times with dichloromethane. The combined extracts are concentrated in vacuo, and the residue is dried under HV. 173 mg (0.242 mmol, 68% of theory) of amorphous beige solid are obtained.

$^1$H-NMR (400 MHz, CDCl$_3$): two sets of signals owing to presence of two rotamers (ratio about 2:1) of the amide function. Signals of the main rotamer are identified by (*), and signals of the subsidiary rotamer by (#).

Unidentified signals are ascribed to overlapping rotamer signals. δ=−0.28 (#, s, 3H, Si—CH$_3$), −0.18 (*, s, 3H, Si—CH$_3$), −0.14 (#, s, 3H, Si—CH$_3$), −0.02 (*, s, 3H, Si—CH$_3$), 0.67 (*, d, 3H, CHCH$_3$), 0.71 (#, s, 9H, tBu), 0.74 (#, d, 3H, CHCH$_3$), 0.84 (*, s, 9H, tBu), 1.4-2.05 (m, 5H, CH and 2×CH$_2$), 2.30 (*, s, 3H, NCH$_3$), 2.5 (s, very broad, 3H, NH$_2$ and NH), 2.84 (#, s, 3H, NCH$_3$), 3.07 (*, ~qui, 1H, NHCH), 3.20 (#. ~qui, 1H, NHCH), 3.55 (#, AB system, 2H, CH$_2$NH$_2$), 3.66 (*, s, 2H, CH$_2$NH$_2$), 3.72 (*, s, 3H, OCH$_3$), 3.76 (#, s, 3H, OCH$_3$), 4.07-4.19 and 4.35-4.72 (m, 4H, CHCH$_3$, CHOH and CHOSi), 6.43 and 6.73-7.43 (m, 17H, arom.-H). A special pulse program (2D EXSY; see Braun, Kalinowski, Berger "150 And More Basic NMR Experiments", Experiment 10.23, page 420, second expanded edition, Wiley-VCH Verlag GmbH, Weinheim 1998) is used to demonstrate that the protons of the two sets of signals mutually interconvert, and thus that rotamers and not stereoisomers are present.

MS (infusion on the Quattroultima, TOF, positive ESI): m/z=714 (63%, M+H$^+$), 697 (100%, M+H$^+$—NH$_3$).

EXAMPLE 7

[2(S)-Hydroxy-1(S)-methyl-2-phenylethyl]-N-methyl-2(R)-[(4-aminomethyl-phenylamino)-(4-methoxyphenyl)-(S)-methyl]-5(S)-(tert-butyldimethylsilanyloxy)-5-(4-fluorophenyl)pentanamide] ("Imine-deprotected Mannich Product")

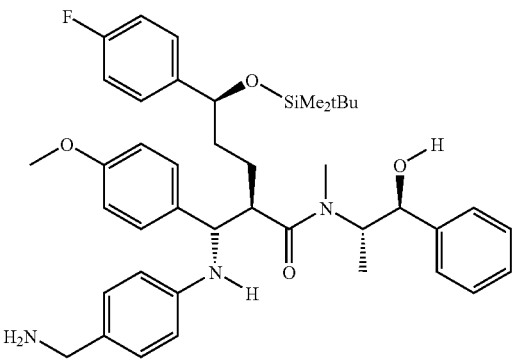

7.6 ml of 20% strength acetic acid/sodium acetate buffer (pH 4.5) are added dropwise to a clear yellow solution of 1.47 g (1.76 mmol) of chromatographically purified imine-protected Mannich product in 7.6 ml of methanol with magnetic stirring under nitrogen. During this, the precursor briefly separates out as an oil but redissolves after a few seconds. A clear solution of pH 5 is obtained. HPLC after stirring at room temperature for 5 minutes shows anisaldehyde and quantitative conversion into the product. After stirring for 30 minutes, the solution is diluted with 45 ml of water, when it becomes cloudy, and adjusted to pH 4 with 0.1 ml of glacial acetic acid. The anisaldehyde is completely removed by extraction with 4×30 ml of n-heptane. 30 ml of dichloromethane are added to the acidic aqueous phase, and the pH is adjusted to 11 while stirring vigorously with 19.5 ml of 1N aqueous sodium hydroxide solution. The organic phase is separated off, and the aqueous phase is extracted with 2×30 ml of dichloromethane. The combined dichloromethane extracts are dried over sodium sulfate, filtered, concentrated in vacuo, and the residue is dried under HV. 1.09 g (1.53 mmol, 87% of theory) of pure product are obtained as an amorphous beige solid.

Complete removal of the anisaldehyde before basification of the aqueous phase is essential. If residues of anisaldehyde remain, the corresponding amount of the precursor is reformed.

EXAMPLE 8

2(R)-[(4-Aminomethylphenylamino)-(4-methoxyphenyl)-(S)-methyl]-5-(4-fluorophenyl)-5(S)-hydroxypentanoic Acid

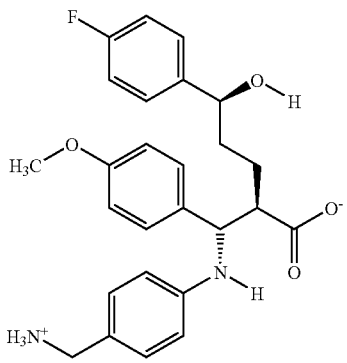

10 ml of ethanol and 4 ml (12.9 mmol) of 3.22N aqueous sodium hydroxide solution are added to 2.09 g (2.5 mmol) of chromatographically purified amide (from Example 5) in a three-neck pear-shaped flask with stirring bar. The mixture is heated to reflux and slowly becomes a clear solution. HPLC check (system as in Example 5, det. 254 nm) after 23 h shows in addition to precursor (t$_{ret}$ 19.4 min.) and imine-deprotected precursor (t$_{ret}$ 18.6 min.) [together 57 area %] mainly anisaldehyde (t$_{ret}$ 9.1 min., 5 area %), pseudoephedrine (t$_{ret}$ 4.2 min., 210 nm), and two product peaks with t$_{ret}$ 6.9 and 6.5 min. (together 26 area %, ratio 4.8:1) which are to be assigned to the product and its epimer (base-induced epimerization of the a position to the carboxy group). A further 4 ml (12.9 mmol) of 3.22N aqueous sodium hydroxide solution are added, and the mixture is refluxed for a further 2 days. The mixture is cooled and the ethanol is removed in vacuo. The aqueous residue is mixed with 25 ml of water and again concentrated in vacuo to a total volume of about 25 ml. The aqueous residue is washed with 3×40 ml of diethyl ether. HPLC analyses show that the ether phases contain uncleaved precursors and anisaldehyde, while more than 90 area % of the acidic aqueous phase comprises the product and its epimer (ratio 4.3:1). 50 ml of dichloromethane are added to the aqueous phase and, while stirring vigorously, the pH is adjusted to 7 with about 8 ml of 2N hydrochloric acid, whereupon a fine precipitate separates out. It is filtered off with suction, washed with water and dichloromethane and dried under HV. 850 mg (1.88 mmol, 75% of theory) of yellowish powder are obtained.

HPLC analysis of the powder shows a ratio of product to epimer of 6:1 and a chemical purity of 93 area %.

$^1$H-NMR and MS data correspond to those for the (purer) product of Example 10.

EXAMPLE 9

2(R)-[(4-Aminomethylphenylamino)-(4-methoxyphenyl)-(S)-methyl]-5-(4-fluorophenyl)-5(S)-hydroxypentanoic Acid

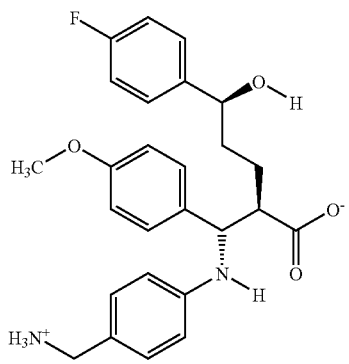

0.8 ml of N-methyl-2-pyrrolidinone and 0.98 ml (5.98 mmol) of 40% strength aqueous tetrabutylammonium hydroxide solution are added to 209 mg (0.25 mmol) of chromatographically purified amide (from Example 5) in a round-bottom flask with stirring bar. The reaction mixture is heated to 40° C. HPLC checks (system as in Example 5, det. 254 nm) show 30% precursor still remaining after 1 h and complete conversion of the precursor after 3 h. The peaks of the product and of the epimer have the same retention time as in Example 8 and their ratio was 5:1.

EXAMPLE 10

2(R)-[(4-Aminomethylphenylamino)-(4-methoxyphenyl)-(S)-methyl]-5-(4-fluorophenyl)-5(S)-hydroxypentanoic Acid

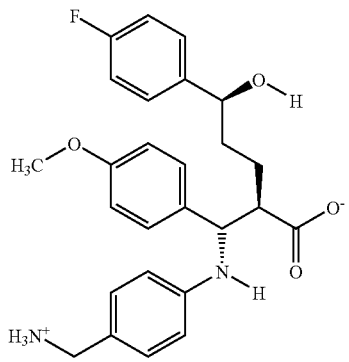

A clear yellow solution of 750 mg (1.05 mmol) of pure imine-deprotected Mannich product (from Example 7) in 12 ml of ethanol is heated to 75° C. in a three-neck pear-shaped flask with stirring bar, and 9 ml (29 mmol) of 3.22 N sodium hydroxide solution are slowly added dropwise while maintaining the internal temperature until a slight turbidity persists. The mixture is then heated to reflux for 19 h. HPLC check (system as in Example 5, det. 254 nm) shows the two product signals (total 90 area %) in the ratio 5:1, also 3.6 area % unreacted precursor, and (at 210 nm) eliminated pseudoephedrine. The reaction mixture is cooled, 20 ml of water are added, and the volume is then concentrated in vacuo to a total of about 20 ml in order to remove the ethanol. 20 ml of water are again added to the aqueous residue, which is again concentrated. The cloudy aqueous residue is washed with 2×20 ml of diethyl ether and then, according to HPLC analysis, contains the products in a purity of 96 area % and in a ratio of 5:1. The aqueous phase is adjusted in an ice bath to pH 7 with 14 ml of 2 N hydrochloric acid, with a flocculent yellow precipitate separating out soon after starting the addition. 10 ml of dichloromethane are added while stirring vigorously, whereupon the precipitate is converted into fine particles. It is filtered off with suction, washed with dichloromethane and a little water and dried under HV. Yield: 340 mg (0.75 mmol, 72% of theory) of pale yellow powder which, according to HPLC, contains the products in a purity of 95 area % and in a ratio of 91:9.

$^1$H-NMR (400 MHz, DMSO-$d_6$): δ=1.14-1.60 (m, 4H, 2×CH$_2$), 2.38 (m, 1H, C$\underline{H}$CO$_2$), 2.7-4.2 (s, very broad, 3-4H, NH$_2$, NH and possibly OH), 3.63 (s, 2H, CH$_2$N), 3.68 (s, 3H, OCH$_3$), 4.21 (d, 1H, NC$\underline{H}$), 4.37 (t, 1H, C$\underline{H}$OH), 6.32 (d, 2H, arom.-H), 6.74 (d, 2H, arom.-H), 6.98 (d, 2H, arom.-H), 7.04 (t, 2H, arom.-H), 7.12-7.28 (m, 4H, arom.-H). MS (infusion at pH 7, Quattroultima TOF, positive ESI): m/z=453 [3%, M+H$^+$ of C$_{26}$H$_{29}$FN$_2$O$_4$], 436 [100%, M+H$^+$—NH$_3$].

EXAMPLE 11 tert-Butyldimethylsilyl 2(R)-[(4-{[(tert-butyldimethylsilanyl)amino]-methyl}phenylamino)-(4-methoxyphenyl)-(S)-methyl]-5(S)-(tert-butyl-dimethylsilanyloxy)-5-(4-fluorophenyl)pentanoate

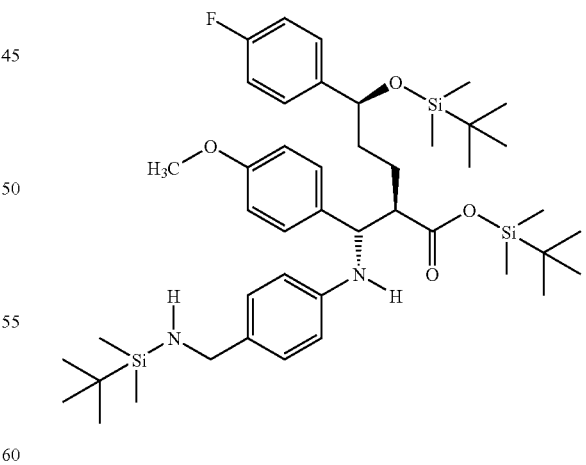

311 mg (0.687 mmol) of the amino hydroxyl carboxylic acid (from Example 10) are suspended in 2 ml of dichloromethane in a 3-neck pear-shaped flask with magnetic stirrer, thermometer and reflux condenser. 272 mg (3.94 mmol) of 99% pure imidazole are added and dissolved. Then a solution of 306 mg (1.97 mmol, 2.9 equivalents) of 97% pure tert-butyldimethylchlorosilane (TBDMS-Cl) in 0.5 ml of dichloromethane is added dropwise. A clear yellow solution forms and is heated to reflux for 4 h. HPLC (system as in Example 5, det. 254 nm) shows the product with $t_{ret}$ 11.7 min and a content of 99.0 area %. The mixture is cooled in an ice bath and, while stirring vigorously, 3 ml of water are added. The phases are separated, and the aqueous phase is extracted with 2×5 ml of dichloromethane. The combined organic phases, cloudy due to insoluble imidazole, are dried over sodium sulfate, filtered, concentrated in vacuo, and the residue is dried under HV, during which the initially resinous solid disintegrates to give an amorphous yellow powder. Yield: 529 mg (0.665 mmol, 97% of theory).

$^1$H-NMR (400 MHz, DMSO-d$_6$): δ=−0.25 (s, 3H, Si—CH$_3$), −0.12 (s, 3H, Si—CH$_3$), −0.03 (s, 6H, Si(CH$_3$)$_2$), 0.02 (s, 6H, Si(CH$_3$)$_2$), 0.71 (s, 9H, Si-tBu), 0.85 (s, 9H, Si-tBu), 0.86 (s, 9H, Si-tBu), 1.07-1.53 (m, 4H, 2×CH$_2$), 2.38 (t, 1H, CHCO$_2$), 3.64 (s, 2H, NCH$_2$), 3.68 (s, 3H, OCH$_3$), 4.25 (d, 1H, NCH), 4.52 (t, 1H, CHOSi), 6.40 (d, 2H, arom.-H), 6.77 (d, 2H, arom.-H), 6.98 (d, 2H, arom.-H), 7.06 (t, 2H, arom.-H), 7.19 (t, 2H, arom.-H), 7.24 (d, 2H, arom.-H). According to NMR, 3.9% by weight (32 mol %) of imidazole are present as impurity.

MS (infusion at pH 7, Quattroultima TOF, negative ESI): m/z=679 (81%, M−H$^-$ of the disilyl compound), 565 (100%, M−H$^-$ of the monosilyl compound). Thus, monosilyl compound (O-TBDMS, —CO$_2$H, —NH$_2$) and disilyl compound (O-TBDMS, CO$_2$H, —NH-TBDMS) is found. The molecular peak of the trisilyl compound cannot be detected because the silyl ester group is too unstable under MS conditions.

EXAMPLE 12

2(R)-[(4-Aminomethylphenylamino)-(4-methoxyphenyl)-(S)-methyl]-5(S)-(tert-butyldimethylsilanyloxy)-5-(4-fluorophenyl)pentanoic Acid

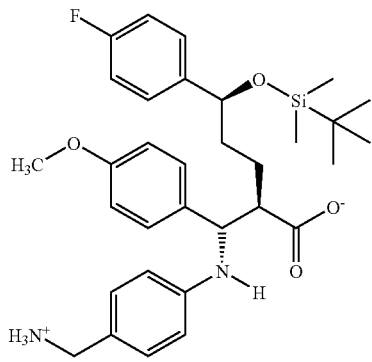

72 μl of glacial acetic acid (Merck) are dissolved in methanol in a 10 ml graduated cylinder and made up to the mark with methanol.

200 mg (0.241 mmol) of the 96% pure Tris-TBDMS compound (from Example 11) are dissolved in 1.0 ml of the methanolic glacial acetic acid solution in a round-bottom flask with magnetic stirrer under nitrogen. The mixture is stirred at room temperature for 2 h and is then concentrated in vacuo, and the residue is dried under HV. $^1$H-NMR analysis (400 MHz, CDCl$_3$) of a sample reveals that the benzylic TBDMS ether function undergoes no deprotection at all, while the TBDMS ester is about 70% and the TBDMS amine is about 35% deprotected. The residue (189 mg) is dissolved in 1.0 ml of the methanolic glacial acetic acid solution, stirred at room temperature for 18 h and then evaporated to dryness as previously. $^1$H-NMR of a sample reveals no deprotection at all of the TBDMS ether, about 85% deprotection of the TBDMS ester and about 43% deprotection of the TBDMS amine. The amount of acetic acid is thus insufficient for sufficiently rapid deprotection of the TBDMS ester and amine. The two NMR solutions are combined with the residue and evaporated to dryness. 200 mg of solid yellow foam are obtained.

210 ml of glacial acetic acid are dissolved in methanol in a further 10 ml measuring cylinder and made up to the mark with methanol.

The above 200 mg of residue are dissolved under nitrogen in 1.0 ml of the methanolic glacial acetic acid solution, heated at a bath temperature of 40° C. for 3 h, left to stand at room temperature overnight and then again heated at 40° C. for 2 h. All the volatile constituents are removed under HV. Residue: 197 mg of solid yellow foam. $^1$H-NMR of a sample reveals no deprotection at all of the TBDMS ether, almost complete deprotection of the TBDMS ester and about 90% deprotection of the TBDMS amine.

$^1$H-NMR (400 MHz, CDCl$_3$): δ=−0.27 (s, 3H, Si—CH$_3$), −0.12 (s, 3H, Si—CH$_3$), 0.73 (s, 9H, Si-tBu), 1.40-1.67 (m, 4H, 2×CH$_2$), 2.41 (broad, 1H, CH—CO$_2$), 3.69 (AB system, 2H, NCH$_2$), 3.80 (s, 3H, OCH$_3$), 4.12 (broad, 1H, NCH), 4.41 (t, 1H, CH—OSi), 6.20 (broad, 2H, arom.-H), 6.75-7.23 (m, 10H, arom.-H)). MS (infusion at pH 7, Quattroultima TOF, positive ESI): m/z=567 (100%, M+H$^+$).

EXAMPLE 13

Methyl 2(R)-[(4-aminomethylphenylamino)-(4-methoxyphenyl)-(S)-methyl]-5(S)-(tert-butyldimethylsilanyloxy)-5-(4-fluorophenyl)pentanoate

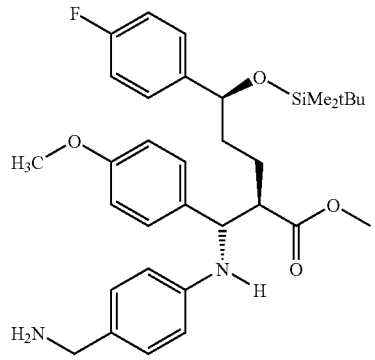

An approximately 0.25 M solution of diazomethane in diethylether (alcohol free) is generated in a diazomethane generator manufactured by Aldrich from N-methyl-N-nitroso-p-toluenesulfonamide (diazogen) in accordance with Aldrich Technical Bulletin No. AL-113, and freshly distilled.

5 ml of the ethereal diazomethane solution are added to a solution of 190 mg of the crude carboxylic acid (from Example 12, i.e. 0.229 mmol) in 1.0 ml of methanol while swirling. An HPLC check (system as in Example 5, det. 254 nm) shows almost complete reaction of the precursor (0.5 area % remaining, $t_{ret}$ 11.7 min.) and clean formation of the monosilylated methyl ester (92 area %, $t_{ret}$ 17.8 min.) and of the disilylated methyl ester (6 area %, $t_{ret}$ 19.8 min). Excess diazomethane and most of the solvents are evaporated by means of a stream of nitrogen blown over the solution. The residue is evaporated to dryness under HV and affords 161 mg of solid yellow resin. The crude product is flash chromatographed [20 g of Merck silica gel 60, 0.04-0.063 mm; condition in a column with EtOAc/MeOH 99:1+1% NEt₃ mobile phase, then elute with 100 ml of this mobile phase, followed by 200 ml of EtOAc/MeOH 98:2+1% NEt₃. Collect in 10 ml fractions. The product is eluted in fractions 9 to 26].

Yield: 105 mg (181 mmol, 79% of theory over 2 stages based on trisilyl compound) of solid yellow foam.

¹H-NMR (400 MHz, CDCl₃): δ=−0.23 (s, 3H, Si—CH₃), −0.09 (s, 3H, Si—CH₃), 0.78 (s, 9H, Si-tBu), 1.5-2.0 (m, 6H, 2×CH₂, NH₂), 2.62 (t, 1H, CH—CO₂Me), 3.58 (s, 3H, CO₂CH₃), 3.66 (s, 2H, NCH₂), 3.77 (s, 3H, OCH₃), 4.38 (s broad, 1H, NH), 4.45 and 4.53 (m and dd, 2×1H, CH—OSi and NCH), 6.48 (d, 2H, arom.-H), 6.80 (d, 2H, arom.-H), 6.90-7.05 (m, 4H, arom.-H), 7.10-7.20 (m, 4H, arom.-H). MS (infusion at pH 7, TOF, positive ESI): m/z=581 (23%, M+H⁺), 564 (100%, M+H⁺—NH₃).

EXAMPLE 14

Methyl 5(S)-(tert-butyldimethylsilanyloxy)-5-(4-fluorophenyl)-2(R)-[(4-{[(4-methoxybenzylidene)amino]methyl}phenylamino)-(4-methoxyphenyl)-(S)-methyl]pentanoate

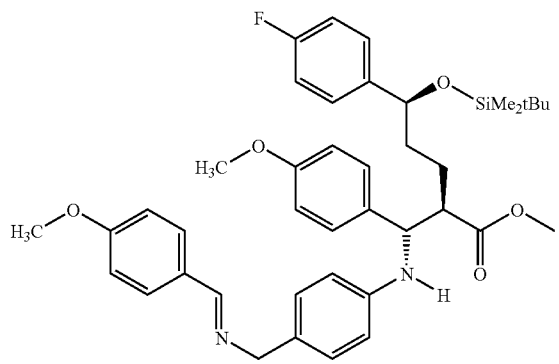

A solution of 95 mg (0.163 mmol) of chromatographed methyl ester (from Example 13) and 22 □l (0.178 mmol) of 98% pure p-anisaldehyde in 3 ml of toluene is concentrated in vacuo in a rotary evaporator at 30° C. The residue is dissolved twice more in 3 ml portions of toluene and again evaporated to dryness each time. An HPLC check (system as in Example 5, det. 254 nm) on a sample shows 92% conversion of the precursor (t_{ret} 18.0 min.) to the product (t_{ret} 19.3 min.), and weak peaks for anisaldehyde (t_{ret} 9.1 min.) and toluene (t_{ret} 12.6 min.). The viscous yellow oil is dried to constant weight under HV.

Yield: 110 mg (0.157 mmol, 96% of theory)

¹H-NMR (400 MHz, CDCl₃): δ=−0.23 (s, 3H, Si—CH₃), −0.09 (s, 3H, Si—CH₃), 0.77 (s, 9H, Si-tBu), 1.44-1.75 (m, 5H, 2×CH₂, NH), 2.61 (m, 1H, CH—CO₂Me), 3.57 (s, 3H, CO₂CH₃), 3.76 (s, 3H, OCH₃), 3.82 (s, 3H, OCH₃), 4.42 (d, 1H, N—CH), 4.50 (dd, broad, 1H, CH—OSi), 4.59 (s, 2H, N—CH₂), 6.47 (d, 2H, arom.-H), 6.79 (d, 2H, arom,—H), 6.89 (d, 2H, arom.-H), 6.94 (t, 2H, arom.-H), 7.00 (d, 2H, arom.-H), 7.09-7.20 (m, 4H, arom.-H), 7.66 (d, 2H, arom.-H), 8.22 (s,1H, N=CH).

EXAMPLE 15

3(R)-[3(S)-(tert-Butyldimethylsilanoyloxy)-3-(4-fluorophenyl)propyl]-1-(4-{[(4-methoxybenzylidene)amino]methyl}phenyl)-4(S)-(4-methoxyphenyl)azetidin-2-one

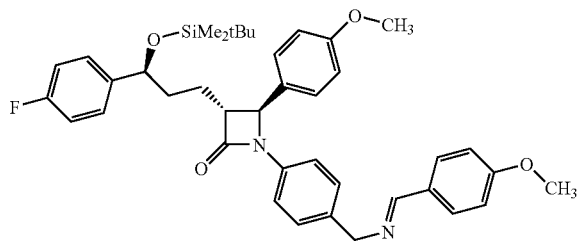

135 μl (0.143 mmol) of a 1.06 M solution of lithium bis(trimethylsilyl)amide in THF are added under nitrogen to a solution of 100 mg (0.143 mmol) of the crude imine-protected methyl ester (from Example 14) in 1.8 ml of absolute THF at −20° C. in a thoroughly heat-dried round-bottom flask with magnetic stirrer. The reaction solution becomes yellow in color. It is stirred for 1 h, during which the temperature rises to −10° C. An HPLC check (system as in Example 5, det. 254 nm) shows 66% clean conversion of the precursor (t_{ret} 19.4 min.) to the product (t_{ret} 19.9 min.) The product moreover cochromatographs with an authentic sample from reference example 1. A further 135 μl (0.143 mmol) of 1.06 M solution of lithium bis(trimethylsilyl)amide in THF is added to the reaction solution at −15° C. An HPLC check now shows complete conversion of the precursor into the product. The reaction mixture is mixed with 3 ml of saturated aqueous sodium bicarbonate solution and extracted with 3×3 ml of dichloromethane. The organic phase is filtered, concentrated in vacuo, and the residue is dried under HV. Yield: 90 mg (0.135 mmol, 94% of theory) of yellow solid.

¹H-NMR (400 MHz, CDCl₃): δ=−0.14 (s, 3H, Si—CH₃), 0.03 (s, 3H, Si—CH₃), 0.90 (s, 9H, Si-tBu), 1.75-2.00 (m, 5H, 2×CH₂, CH—CO—N), 3.02 (m, 1H, N—CH), 3.81 (s, 3H, OCH₃), 3.86 (s, 3H, OCH₃), 4.52-4.74 (m, 3H, CH—OSi, N—CH₂), 6.88 (d, 2H, arom.-H), 6.93 (d, 2H, arom.-H), 7.00 (t, 2H, arom.-H), 7.16-7.27 (m, 8H, arom.-H), 7.70 (d, 2H, arom.-H), 8.28 (s, 1H, N=CH). MS (infusion at pH 7, TOF, positive ESI): m/z=667 (100%, M+H⁺), 532 (5%, M+H⁺—CH₃O—C₆H₄—CH=NH]. ¹H-NMR and MS, and UV spectrum and t_{ret} in HPLC, are identical to the authentic comparison substance from reference example 1.

EXAMPLE 16

1-(4-Aminomethylphenyl)-3(R)-[3(S)-(tert-butyldimethylsilanyloxy)-3-(4-fluorophenyl)propyl]-4(S)-(4-methoxyphenyl)azetidin-2-one

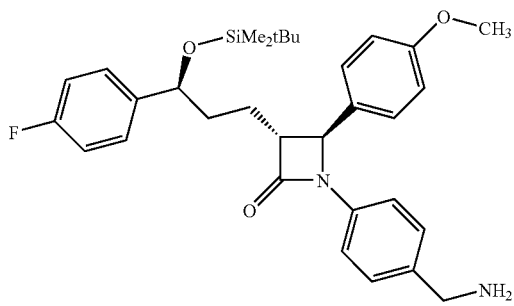

Elimination of the imino protective group takes place in analogy to Example 6 by dissolving imine-protected β-lactam (from Example 15) in acetonitrile/water/glacial acetic acid and semipreparative HPLC of this solution.

Analytical HPLC (system as in Example 5): the precursor ($t_{ret}$ 19.9 min.) is completely converted into the product ($t_{ret}$ 17.1 min.).

$^1$H-NMR (400 MHz, DMSO-$d_6$): δ=−0.16 (s, 3H, Si—CH$_3$), 0.02 (s, 3H, Si—CH$_3$), 0.87 (s, 9H, Si-tBu), 1.76 (m, 4H, 2×CH$_2$), 2.10 (very broad, 1H, CH—CO—N), 3.06 (m, 1H, N—CH), 3.60 (s, 2H, N—CH$_2$), 3.73 (s, 3H, OCH$_3$), 4.37 (s, broad, 2H, NH$_2$), 4.76 (m, 1H, CH—OSi), 6.92 (d, 2H, arom.-H), 7.10-7.18 (m, 4H, arom.-H), 7.21 (d, 2H, arom.-H), 7.28-7.38 (m, 4H, arom.-H). The spectrum is identical to that of an authentic sample prepared in accordance with the information in WO 02/50027.

EXAMPLE 17

1-(4-Aminomethylphenyl)-3(R)-[3(S)-hydroxy-3-(4-fluorophenyl)propyl]-4(S)-(4-methoxyphenyl)azetidin-2-one

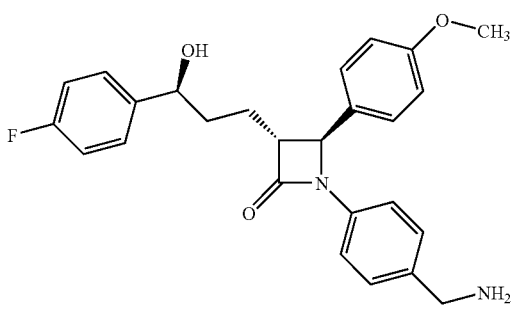

0.5 ml (3.57 mmol) of 50% strength aqueous sulfuric acid is added dropwise to a solution, cooled in ice, of 70 mg (0.105 mmol) of the crude, protected β-lactam (from Example 15) in 0.5 ml of 1,4 dioxane under nitrogen. Since an oil separates out, the mixture is allowed to warm to room temperature, and a further 1.0 ml of 1,4 dioxane is added, resulting in a clear yellow solution again. HPLC (system as in Example 5, 254 nm) of a sample after 5 min shows formation of the product (36 area %, $t_{ret}$ 8.9 min.) and anisaldehyde (21 area %, $t_{ret}$ 9.1 min.), in addition to the partially deprotected intermediate (6 area %, $t_{ret}$ 16.9 min.) and unreacted precursor (18 area %, $t_{ret}$ 20.0 min.). HPLC of a sample after 35 min shows quantitative conversion of the precursor.

HPLC-MS (TOF, positive ESI): m/z=418 (100%, M+H$^+$—NH$_3$).

EXAMPLE 18

Methyl 5(S)-(4-fluorophenyl)-5-[tetrahydropyran-2(RS)-yloxy]pentanoate

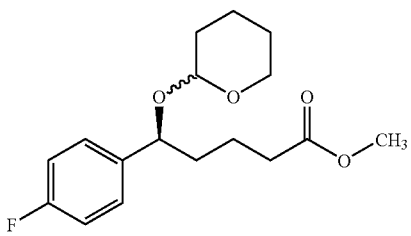

4.23 ml (45 mmol) of 97% pure 3,4-dihydro-2H-pyran, followed by 762 mg (3.0 mmol) of pyridinium p-toluenesulfonate are added to a solution of 6.80 g (25.8 mmol) of methyl 5-(4-fluorophenyl)-5-(S)-hydroxypentanoate with a purity of 86 area % in 210 ml of dichloromethane in a 2-neck round-bottom flask with magnetic stirrer under nitrogen. The reaction mixture is stirred at room temperature for 24 h. HPLC analysis (system as in Example 5) shows besides pyridine ($t_{ret}$ 4.8 min.) and 1.5 area % precursor ($t_{ret}$ 9.8 min.), the product in the form of two diastereomers (ratio about 1:1, $t_{ret}$ 14.1 and 14.4 min.). The reaction solution is concentrated to 70 ml in vacuo, diluted with 100 ml of diethyl ether and washed with 1×100 ml and 2×50 ml of water. The organic phase was concentrated in vacuo and the residue was dried under HV. 9.70 g of a pale yellowish oil which, according to HPLC, has a purity of 76 area % are obtained. Yield: 23.75 mmol, 92% of theory.

$^1$H-NMR (400 MHz, CDCl$_3$): δ=1.4-1.9 (m, 10H, 5×CH$_2$), 2.32 (m, 2H, CH$_2$—C=O), 3.27 (dt, 0.5H, O—CH, one diastereomer), 3.50 (m, 1H, O—CH, both diastereomers), 3.64 (s, 3H, CO$_2$CH$_3$), 3.91 (m, 0.5H, O—CH, one diastereomer), 4.35 (t, 0.5H, O—CH—O, one diastereomer), 4.56 (t, 0.5H, aryl-CH—O, one diastereomer), 4.67 (dd, 0.5H, aryl-CH—O, one diastereomer), 4.80 (t, 0.5H, O—CH—O, one diastereomer), 7.01 (m, 2H, arom.-H), 7.22-7.34 (m, 2H, arom.-H). HPLC-MS (Quattroultima, positive ESI): both diastereomers show m/z=328 (M+NH$_4^+$, intensity 60-80%) and m/z=209 (M+H$^+$-2-hydroxy-THP, intensity 100%).

EXAMPLE 19

Methyl 5(S)-(4-fluorophenyl)-5-trityloxypentanoate

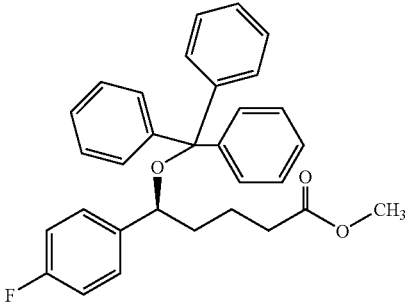

13.6 g (51.7 mmol) of methyl 5-(4-fluorophenyl)-5-(S)-hydroxypentanoate with a purity of 86% area %, 18.1 g (63.0 mmol) of 97% pure triphenylchloromethane, 12.0 ml (89.9 mmol) of 99% pure 2,4,6-collidine and 23.8 g (63.1 mmol) of 98% pure tetrabutylammonium iodide are dissolved in 36 ml of dichloromethane in a 3-neck flask with magnetic stirrer and septum, and the reaction mixture is boiled under reflux under nitrogen for 12 hours (internal temp. 57° C.). HPLC analysis (system as in Example 5) shows besides collidine ($t_{ret}$ 8.1 min.) and trityl chloride ($t_{ret}$ 14.3 min.), product ($t_{ret}$ 17.8 min.) and traces of precursor ($t_{ret}$ 9.8 min.). The mixture is cooled, diluted with 300 ml of dichloromethane, and washed with 1×200 and 2×100 ml of 10% strength aqueous acetic acid, then with 2×100 ml of saturated aqueous NaHCO$_3$ solution followed by 2×100 ml of water. 100 ml of n-heptane are added to the organic phase (turbidity), which is then concentrated in vacuo. During this, an oil separates out and crystallizes after a short time. The mass of crystals is filtered off with suction and washed with n-heptane and a little isopropanol. The filter cake is triturated with n-heptane and filtered off with suction three more times. The crude product (28 g of brown resin) is filtered through 28 g of silica gel (Baker 30-60 μm) with initially 400 ml of ethyl acetate/n-heptane 98:2 and then 400 ml of 95:5 to remove residues of precursor. 25.4 g of yellow resin with a purity according to HPLC of 85 area % are obtained (11 area % trityl chloride as impurity). Yield: 46.1 mmol, 89% of theory.

$^1$H-NMR (400 MHz, CDCl$_3$): δ=1.15-1.48 (m, 4H, 2×CH$_2$), 2.01 (t, 2H, CH$_2$C=O), 3.58 (s, 3H, CO$_2$CH$_3$), 4.48 (dd, 1H, aryl-CH—O), 6.82 (~t, 2H, arom.-H), 7.02 (~dd, 2H, arom.-H), 7.13-7.23 (m, 9H, arom.-H), 7.43 (~dd, 6H, arom.-H).

HPLC-MS of an analytical sample with a purity of 97 area % obtained by chromatography (TOF, positive ESI): only m/z=243 of the trityl cation is observable. GC-MS (injected in CH$_2$Cl$_2$, det. by CI): only m/z=243 of the trityl cation is observable.

EXAMPLE 20

Methyl 5(S)-ethoxymethoxy-5-(4-fluorophenyl)pentanoate

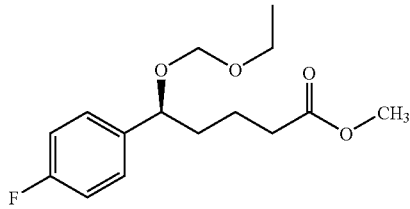

40.6 g of phosphorus pentoxide are added to a vigorously stirred solution of 10.5 g (42.7 mmol) of methyl 5-(4-fluorophenyl)-5-(S)-hydroxypentanoate with a purity of 92% area % (Example 1) in 220 ml of dichloromethane and 152 ml (1200 mmol) of 99% pure diethoxymethane in a 4-neck flask with mechanical stirrer, the internal temperature rising from initially 23° C. to 30° C. There is initial formation of a white suspension whose particles quickly agglomerate and form a viscous mass which partly adheres to the bottom of the flask and changes color via yellow to brown. HPLC analysis (system as in Example 5) shows complete conversion of the precursor (t$_{ret}$ 9.8 min.) into the product (t$_{ret}$ 13.4 min.) after only 5 min. The reaction mixture is stirred at 29° C. without external heating (i.e. continuing exothermic reaction) for 0.5 h, but the only effect of this was to increase an impurity (t$_{ret}$ 13.2 min.). The reaction mixture is cooled to +10° C. in an ice bath, and 100 g of ice are added to the mixture. The viscous solid mass dissolves only slowly even with vigorous stirring. The mixture is transferred into a separating funnel and diluted with 200 ml of diethyl ether. The organic phase is separated off, and the aqueous phase is extracted again with 100 ml of diethyl ether. The combined extracts are washed with 100 ml of saturated aqueous sodium bicarbonate solution and with 100 ml of saturated aqueous sodium chloride solution, and then concentrated in vacuo, and the residue is dried under HV. 13.83 g of brown oil are obtained. The crude product has a GC purity of 84 area %. It is distilled through a silvered 15 cm vacuum-jacketed Vigreux column under HV (0.005 mbar). After a fore-run (1 g, b.p. 33-88° C., colorless mobile oil), the product distills (9.5 g, b.p. 102-103° C., colorless oil) at a bath temperature of 160-170° C., and 3 g of higher-boiling impurity remain as bottom product. Yield: 9.5 g (33.4 mmol), 78% of theory.

$^1$H-NMR (400 MHz, CDCl$_3$): δ=1.18 (t, 3H, C—CH$_3$), 1.56-1.90 (m, 4H, 2×CH$_2$), 2.34 (t, 2H, CH$_2$—C=O), 3.48 (dqua, 1H, CH$_3$—CH$_2$), 3.67 (s, 3H, CO$_2$CH$_3$), 3.72 (dqua, 1H, CH$_3$—CH$_2$), 4.52 (d, 1H, OCH$_2$O), 4.58 (dd, 1H, aryl-CH—O), 4.62 (d, 1H, OCH$_2$O), 7.03 (~t, 2H, arom.-H), 7.29 (~dd, 2H, arom.-H). HPLC-MS (infusion at pH 7 in a Quattroultima, TOF, positive ESI): m/z=302 (20%, M+NH$_4$$^+$), 209 (65%, M+H$^+$—EtOCH$_2$OH). GC-MS (CI): m/z=302 (11%, M+NH$_4$$^+$), 209 (100%, M+H$^+$—EtOCH$_2$OH).

EXAMPLE 21

[2(S)-Hydroxy-1(S)-methyl-2-phenylethyl]-N-methyl-5(S)-(4-fluorophenyl)-5-[tetrahydropyran-2(RS)-yloxy]pentanamide]

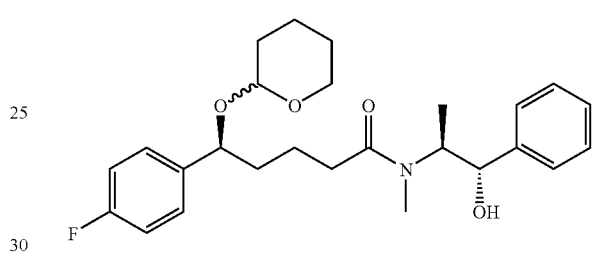

5.3 ml (13.3 mmol) of a 2.5 molar solution of n-butyllithium in hexane are added dropwise by syringe over the course of 10 min to a solution of 2.85 g (66.8 mmol) of anhydrous lithium chloride and of 5.59 g (33.2 mmol) of 98% pure (+)-pseudoephedrine in 46 ml of absolute THF at 0-2° C. in a 250 ml 4-neck round-bottom flask with magnetic stirrer, septum and thermometer under argon, during which the temperature rises to 5-6° C. After 10 min, a solution of 9.31 g (22.8 mmol) of methyl 5(S)-(4-fluorophenyl)-5-[tetrahydropyran-2(RS)-yloxy]pentanoate with a purity of 76 area % (from Example 18) in 9.5 ml of abs. THF is added dropwise over the course of 10 min, allowing the mixture to warm to room temperature. The clear reaction solution is stirred at room temperature for 3 days. HPLC (system as in Example 5) shows besides pseudoephedrine (t$_{ret}$ 4.2 min.) now only traces of the two diastereomeric precursors (t$_{ret}$ 14.1 and 14.4 min.), and formation of the product as pair of diastereomers (t$_{ret}$ 13.3 and 13.5 min.) and of a by product (t$_{ret}$ 9.0 min.). The mixture is cooled with ice, and 45 ml of water are added dropwise, initially very slowly and then more quickly. Two phases form. Most of the THF is distilled off in vacuo. The oil is extracted from the aqueous phase with 3×25 ml of ethyl acetate, adjusting the pH to 6-7 with 6 ml of 10% strength acetic acid in order to achieve an acceptable rate of phase separation. The combined extracts are washed with 20 ml of saturated NaHCO$_3$ solution and with 20 ml of water, and then the solvent is distilled off in vacuo. The residue is dried under HV. 13.0 g of crude product are obtained as a pale yellow voluminous solid foam which has an HPLC purity of 76 area %. Filtration of the crude product through a column of 30 g of silica gel 60 (0.04-0.063 mm) with ethyl acetate/n-heptane 2:8 to 8:2/0.5% triethylamine affords 10.6 g of viscous yellow resin, which is recrystallized from hot diisopropyl ether. The dense mass of crystals is filtered off with suction, washed with a little diisopropyl ether and dried under HV. 9.0 g of granular colorless crystals having an HPLC purity of 95 area % are obtained as a 1:1 diastereomer pair, m.p. 93-95° C. Yield: 19.3 mmol, equivalent to 85% of theory.

$^1$H-NMR (400 MHz, CDCl$_3$): each of the two diastereomers show two sets of signals owing to the presence of 2 rotamers in each ratio about 2.8:1). Signals of the main rotamer have been identified by (*), and signals of the subsidiary rotamer by (#). Unidentified signals are ascribed to overlapping rotamer signals. δ=0.94 (#, 2×d), 1.09 (*, d) and 1.13 (*, d) (3H, C—CH$_3$); 1.38-1.93 (m, 10H, 5×CH$_2$); 2.18-2.55 (m, 2H, CH$_2$—C=O); 2.76 (*), 2.78 (*) and 2.89 (#) (3×s, 3H, N—CH$_3$); 3.27 and 3.92 (dt, 1H, OCH$_2$); 3.48 (m, 1H, OCH$_2$); 3.97 (#) and 4.43 (*) (2×qui, 1H, CHCH$_3$); 4.18 (br., 1H, OH); 4.35 and 4.81 (2×t, 1H, O—CH—O); 4.54 and 4.68 (concealed and dd, 1H, aryl-CH—O); 4.57 (t, 1H, CH—OH); 7.01 (2×t, 2H, arom.-H); 7.22-7.41 (m, 7H, arom.-H). HPLC-MS (Quattroultima, TOF, positive ESI): m/z=444 (58%, M+H$^+$), 360 (100%, M+H$^+$—DHP), 342 (68%, M+H$^+$-THPOH).

EXAMPLE 22

[2(S)-Hydroxy-1(S)-methyl-2-phenylethyl]-N-methyl-5(S)-(4-fluorophenyl)-5-trityloxypentanamide]

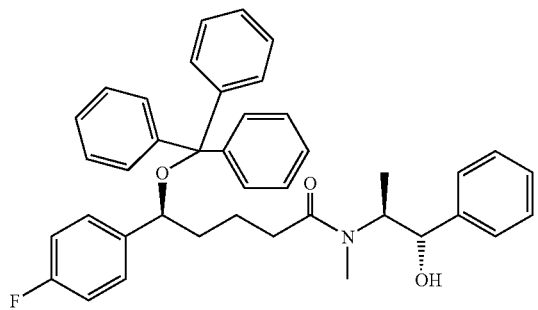

3.97 ml (9.93 mmol) of a 2.5 molar solution of n-butyllithium in hexane are added dropwise by syringe pump over the course of 10 min to a solution of 1.90 g (44.4 mmol) of anhydrous lithium chloride and of 3.74 g (22.2 mmol) of 98% pure (+)-pseudoephedrine in 30 ml of absolute THF at 0-2° C. under argon in a 3-neck flask with magnetic stirrer, septum and thermometer, during which the temperature rises to 5-6° C. After 10 min, a solution of 10.50 g (19.0 mmol) of methyl 5(S)-(4-fluorophenyl)-5-trityloxypentanoate with a purity of 85 area % (from Example 19) in 10 ml of absolute THF is added dropwise over the course of 5 min, allowing the mixture to warm to room temperature. The clear reaction solution is stirred at room temperature for 3 days. HPLC (system as in Example 5) shows besides pseudoephedrine (t$_{ret}$ 4.2 min.) now only traces of the precursor (t$_{ret}$ 17.8 min), and formation of the product (t$_{ret}$ 17.0 min.). The mixture is cooled with ice, and 30 ml of water are added dropwise, initially very slowly and then more quickly. Two phases form. Most of the THF is distilled off in vacuo. The oil is extracted from the aqueous phase with 3×15 ml of ethyl acetate, the pH being adjusted to 6 with 4 ml of 10% strength aqueous acetic acid to achieve an adequate rate of phase separation. The combined extracts are washed with 15 ml of saturated aqueous NaHCO$_3$ solution and with 15 ml of water, and then the solvent is distilled off in vacuo. The residue is dried under HV. 13.2 g of crude product are obtained as a yellow voluminous solid foam which has an HPLC purity of 72 area %. Medium pressure column chromatography [130 g of silica gel 60 (Merck), 0.04-0.063 mm, conditioning with 0.4 l of ethyl acetate/heptane 2:8 plus 0.5% triethylamine, mobile phase 100 ml of ethyl acetate/heptane 2:8 plus 0.5% triethylamine followed by 1 l of ethyl acetate/heptane 1:1 plus 0.5% triethylamine, flow rate 25 ml/min, collection of 20 ml fractions (65 sec)] affords the product as pale yellow resin which has an HPLC purity of 97 area %. Yield: 9.40 g (15.2 mmol) equivalent to 80% of theory.

$^1$H-NMR (400 MHz, CDCl$_3$): the product shows two sets of signals owing to the presence of 2 rotamers (ratio about 2.7:1). Signals of the main rotamer are identified by (*), and signals of the subsidiary rotamer by (#). Unidentified signals are ascribed to overlapping rotamer signals. δ=0.86 (#) and 1.03 (*) (2×d, 3H, C—CH$_3$); 1.16-1.54 (m, 4H, 2×CH$_2$); 1.87-2.04 (*) and 2.04-2.20 (#) (2×m, 2H, CH$_2$—C=O); 2.63 (*) and 2.83 (#) (2×s, 3H, N—CH$_3$); 3.76 (#) and 4.34 (*) (2×~qui, 1H, CHCH$_3$); 4.16 (br s, 1H, OH); 4.45-4.56 (m, 2H, aryl-CH—O and CHOH); 6.76 (#) and 6.80 (*) (2×t, 2H, arom.-H); 7.02 (dd, 2H, arom.-H); 7.12-7.38 (m, 14H, arom.-H); 7.44 (dd, 6H, arom.-H). HPLC-MS (Quattroultima, TOF, positive ESI): m/z=243 (100%, Ph$_3$C$^+$). MS (infusion in Quattroultima, TOF, negative ESI): m/z=660 (100%, M+AcO$^-$).

EXAMPLE 23

[2(S)-Hydroxy-1(S)-methyl-2-phenylethyl]-N-methyl-5(S)-ethoxymethoxy-5-(4-fluorophenyl)pentanamide]

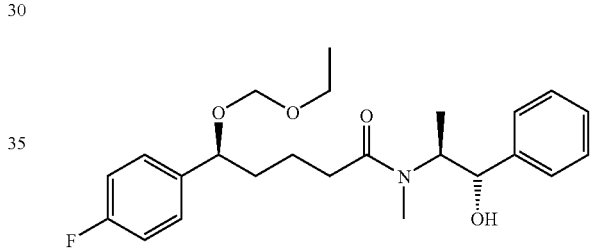

3.56 ml (8.91 mmol) of 2.5 molar solution of n-butyllithium in hexane are added dropwise by syringe pump over the course of 10 min to a solution of 1.91 g (44.7 mmol) of anhydrous lithium chloride and of 3.74 g (22.2 mmol) of 98% pure (+)-pseudoephedrine in 30 ml of absolute THF at 0-2° C. in a 3-neck flask with magnetic stirrer, septum and thermometer under argon. After 10 min, a solution of 5.68 g (18.4 mmol) of methyl 5(S)-ethoxymethoxy-5-(4-fluorophenyl) pentanoate with a purity of 92 area % (from Example 20) in 7.5 ml of abs. THF is added dropwise by syringe pump over the course of 30 min, allowing the mixture to warm to room temperature. The clear reaction solution is stirred at room temperature for 3 days. HPLC (system as in Example 5) showed besides 7 area % pseudoephedrine (t$_{ret}$ 4.2 min.) now traces (<1 area %) of the precursor (t$_{ret}$ 13.4 min.), and formation of the product (68 area %, t$_{ret}$ 12.7 min.). The mixture is cooled with ice, and 30 ml of water are added dropwise, initially very slowly and then more quickly. Two phases form. Most of the THF is distilled off in vacuo, and the oil which separates out is extracted with 1×30 ml and 2×15 ml of ethyl acetate, the pH having been adjusted to 6 with 4 ml of 10% strength aqueous acetic acid to achieve a sufficiently rapid phase separation. The combined organic extracts are washed with 15 ml of saturated aqueous NaHCO$_3$ solution and with 15 ml of water, concentrated in vacuo, and the residue is dried under HV. 8.40 g of a yellowish oil which slowly crystallizes are obtained. The crude product is stirred vigorously and heated to reflux in 10 ml of diisopropyl ether, whereupon most of the solid dissolves. It is slowly cooled to 10° C., the crystals are filtered off with suction and washed with 2 ml of diisopropyl ether, and the crystals are dried under HV. 5.90 g of colorless solid, m.p. 91-92° C., which has a purity of 92 area % according to HPLC analysis are obtained. Yield: 13.00 mmol, equivalent to 71% of theory.

$^1$H-NMR (400 MHz, CDCl$_3$): the product shows two sets of signals owing to the presence of two rotamers (ratio about 2.7:1). Signals of the main rotamer are identified by (*), and signals of the subsidiary rotamer by (#). Unidentified signals are ascribed to overlapping rotamer signals. δ=0.94 (#) and 1.08 (*) (2×d, 3H, C—CH$_3$); 1.15 (#) and 1.16 (*) (2×t, 3H, CH$_2$—CH$_3$); 1.53-1.91 (m, 4H, CH$_2$—CH$_2$); 2.21-2.55 (m, 2H, CH$_2$—C=O); 2.78 (*) and 2.89 (#) (2×s, 3H, N—CH$_3$); 3.46 (m, 1H, OC$\underline{H}$—CH$_3$), 3.70 (m, 1H, OC$\underline{H}$—CH$_3$); 3.95 (#) and 4.44 (*) (2×~qui, 1H, C$\underline{H}$CH$_3$); 4.19 (br s, 1H, OH); 4.51 (d, 1H, O—CH—O); 4.57 (m, 2H, aryl-C$\underline{H}$—O and C $\underline{H}$OH); 4.61 (d, 1H, O—CH—O), 7.01 (~t, 2H, arom.-H); 7.22-7.41 (m, 7H, arom.-H). HPLC-MS (Quattroultima, TOF, positive ESI): m/z=418 (100%, M+H$^+$), 342 (32%, M+H$^+$—EtOCH$_2$OH).

EXAMPLE 24

[2(S)-Hydroxy-1(S)-methyl-2-phenylethyl]-N-methyl-2(R)-[(4-aminomethyl-phenylamino)-(4-methoxyphenyl)-(S)-methyl]-5(S)-[(4-fluorophenyl)-5-[tetrahydropyran-2(RS)-yloxy]pentanamide] (THP-protected, Imine-deprotected Mannich Product")

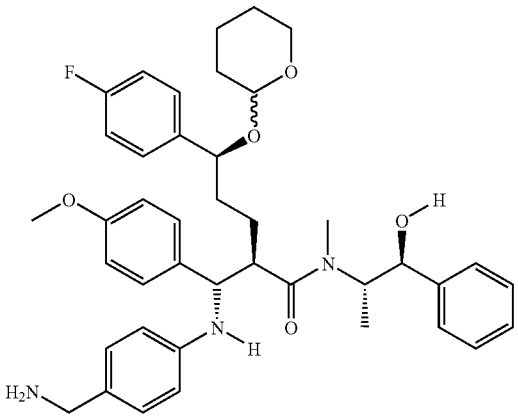

Lithium chloride (99% pure) is dried at 150-200° C./4× 10$^{-3}$ mbar for 3 h. Diisopropylamine (99.5% pure) is distilled fresh from CaH$_2$ and then contains 0.02% by weight water according to Karl-Fischer titration. THF is degassed by bubbling through dried argon and contains <0.005% by weight water according to Karl-Fischer titration.

12.0 ml of THF and 3.2 ml (22.5 mmol) of diisopropylamine are added to 2.53 g (59.1 mmol) of dried lithium chloride in a thoroughly heat-dried 3-neck round-bottom flask with magnetic stirrer, septum, argon inlet and low-temperature thermometer. The mixture is cooled to −78° C. in dry ice/acetone bath, and 8.3 ml (20.8 mmol) of a 2.5 molar solution of n-butyllithium in hexane are added dropwise by syringe pump over the course of 20 min. The mixture is a thick paste. It is allowed to warm to 0° C. and then stirred at 0° C. for 5 min, during which a cloudy solution forms. It is again cooled to −78° C., again resulting in a thick paste which can be stirred only with difficulty. A solution of 4.44 g (9.51 mmol) of the pseudoephedrine amide with a purity of 95 area % (from Example 21) in 20 ml of THF is added dropwise by syringe pump over the course of 20 min. The mixture becomes pale yellow in color, and the solid dissolves. The mixture is stirred at −78° C. for 1 h. It is allowed to warm to 0° C., is stirred at this temperature for 15 min and at room temperature for a further 5 min and is again cooled to 0° C. A solution of 7.17 g (20.0 mmol, 2 equivalents based on amide) of the bisimine (from Example 4) in 24 ml of THF is added dropwise over the course of 10 min, during which the reaction mixture becomes orange in color and, during the subsequent stirring at 0° C. for 3 hours, brown. HPLC monitoring of the course of the reaction (system as in Example 5) shows the imine-protected Mannich product (48 area %) as 1:1 diastereomer pair (t$_{ret}$ 16.3 and 16.7 min.) in addition to unreacted pseudoephedrine amide as diastereomer pair (6 area %; t$_{ret}$ 13.3 and 13.6 min.) and excess diimine (t$_{ret}$ 14.0 min.). The ice-cold reaction mixture is poured with stirring into 112 ml of ice/water under nitrogen, whereupon it becomes yellow in color and two phases form. It is extracted with 1×80 ml and 2×35 ml of dichloromethane. The combined extracts are concentrated in vacuo, and the residue is dried under HV. 12.0 g of yellow amorphous tacky foam comprising, according to HPLC, 45 area % imine-protected Mannich product, 6 area % pseudoephedrine amide (precursor) and diimine are obtained. This crude product is subjected to purification by chromatography with simultaneous elimination of the imine protective group. For this purpose, a glass column (diameter 7.0 cm, length 46 cm) is packed with 1770 ml (about 900 g) of silica gel 60 (Merck, 0.04-0.063 mm) in a Büchi medium-pressure system. The column is conditioned at a flow rate of 130 ml/min. with 1.5 l of CH$_2$Cl$_2$/MeOH/NH$_4$OH (25% strength) 9:1.5:0.3, then with 2 l of CH$_2$Cl$_2$. The crude product, dissolved in 15 ml of CH$_2$Cl$_2$, is then loaded onto the column. Nonpolar impurities are eluted with 1 l of CH$_2$Cl$_2$ followed by 0.5 l of CH$_2$Cl$_2$/MeOH 99:1, followed by 0.5 l of CH$_2$Cl$_2$/MeOH 98:2, followed by 0.5 l of CH$_2$Cl$_2$/MeOH 95:5. The product which undergoes aqueous deprotection on the column is then eluted with 1 l of CH$_2$Cl$_2$/MeOH/NH$_4$OH (25% strength) 9:0.5:0.1, followed by 3 l of CH$_2$Cl$_2$/MeOH/ NH$_4$OH (25% strength) 9:1:0.2 followed by 2 l of CH$_2$Cl$_2$/ MeOH/NH$_4$OH (25% strength) 9:1.5:0.3. Fractions of about 140 ml are taken (filling time 95 sec). Fractions 25-31 are combined with addition with toluene. Azeotropic entrainment of the water by toluene on concentration prevents the product remaining in residues of water from the ammonia, in which it would undergo a retro-Mannich reaction. The solvents are removed in vacuo, and the residue is dried under HV. 4.50 g of beige amorphous gel which has an HPLC purity of >99 area % are obtained.

Yield: 6.51 mmol, equivalent to 68% of theory.

$^1$H-NMR (400 MHz, CDCl$_3$): four sets of signals are present because the product is an approximately 1:1 mixture of diastereomers, owing to the chirality center in the THP protective group, and there are two rotamers (ratio about 3.2:1) of the amide function for each diastereomer. The spectrum is complex, so that uncertainties are involved in the signal assignments. For the same reason, reliable estimation of the diastereoselectivity of the Mannich addition is not possible either by NMR or by HPLC of the reaction product. Signals of the main rotamer have been identified by (*), and signals of the subsidiary rotamer by (#). Unidentified signals are ascribed either to overlapping rotamer signals or cannot be assigned unambiguously to a particular rotamer because of the complexity of the spectrum. δ=0.67 (*), 0.67 (*), 0.81 (#), 0.83 (#) (4×d, 3H, C—CH$_3$); 1.30-2.13 (m, 13-14H, 5×CH$_2$, C<u>H</u>—C=O, NH₂, possibly also OH); 2.29 (*), 2.34 (*), 2.83 (#) (3×s, 3H, NCH₃; 3.07-3.50 (m, 2H, C<u>H</u>—NHaryl, O—C<u>H</u>—CH₂); 3.58 (#), 3.64 (*) (2×s, broadened, 2H, C<u>H</u>₂NH₂); 3.73 (*), 3.73 (*), 3.75 (#) (3×s, 3H, OCH₃); approx. 3.75-3.91 (m, 1H, O—C<u>H</u>—CH₂); 4.05-4.79 (m, 4-5H, C<u>H</u>CH₃, C<u>H</u>OH, C<u>H</u>OTHP, OC<u>H</u>O, possibly also OH); 5.94 (#), 5.98 (*) (2×t, partially concealed, 1H, arom.-H); 6.41 (*), 6.43 (*), 6.44 (#), 6.46 (#) (4×d, 2H, arom.-H); 6.75, 6.77 (2×d, 2H, arom.-H); 6.84-7.44 (m, 13H, arom.-H). HPLC-MS (Quattroultima, TOF, positive ESI): two diastereomeric products (ratio 1:1, t_ret 14.38 and 14.81 min.), both show m/z=684 (100%, M+H⁺), 667 (respectively 22% and 15%, M+H⁺—NH₃), 583 (respectively 68% and 61%, M+H⁺—THP—O.). MS (infusion in Quattroultima, TOF, positive ESI): m/z=684 (100%, M+H⁺), 667 (76%, M+H⁺—NH₃).

EXAMPLE 25

[2(S)-Hydroxy-1(S)-methyl-2-phenylethyl]-N-methyl-2(R)-[(4-aminomethyl-phenylamino)-(4-methoxyphenyl)-(S)-methyl]-5(S)-[(4-fluorophenyl)-5-trityloxy]pentanamide] (Trityl-protected, Imine-deprotected Mannich Product")

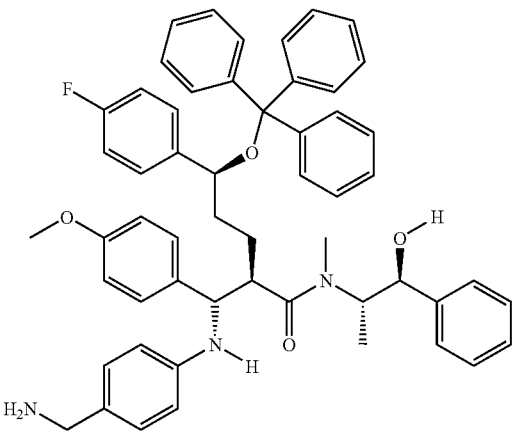

Lithium chloride (99% pure) is dried at 150-200° C./4× 10⁻³ mbar for 3 h. Diisopropylamine (99.5% pure) is distilled fresh from CaH₂ and then contains 0.02% by weight water according to Karl-Fischer titration. THF is degassed by bubbling through dried argon and contains <0.005% by weight water according to Karl-Fischer titration.

12.0 ml of THF and 3.2 ml (22.5 mmol) of diisopropylamine are added to 2.53 g (59.1 mmol) of dried lithium chloride in a thoroughly heat-dried 250 ml four-neck round-bottom flask with magnetic stirrer, septum, argon inlet and low-temperature thermometer. The mixture is cooled to −78° C. in a dry ice/acetone bath, and 8.3 ml (20.8 mmol) of a 2.5 molar solution of n-butyllithium in hexane are added dropwise by syringe pump over the course of 20 min. The mixture is a thick paste. It is allowed to warm to 0° C. and then stirred at 0° C. for 5 min, during which a cloudy solution forms. It is again cooled to −78° C., and then a solution of 6.02 g (9.70 mmol) of the pseudoephedrine amide with a purity of 97 area % (from Example 22) in 20 ml of THF is added dropwise by syringe pump over 20 min, during which the mixture becomes ocher in color. It is then stirred at −78° C. for 1 h. It is allowed to warm to 0° C. and stirred at this temperature for 15 min and at room temperature for a further 5 min, and is again cooled to 0° C. A solution of 7.17 g (20.0 mmol, 2 equivalents based on amide) of the bisimine (from Example 4) into 24 ml of THF is added dropwise over the course of 10 min, during which the reaction mixture becomes dark brown in color. It is stirred at 0° C. for 2.5 hours. HPLC monitoring of the course of the reaction (system as in Example 5) shows after 1 hour the imine-protected Mannich product (47 area %, t_ret 18.7 min.) in addition to unreacted precursor (5.7 area %; t_ret 17.06 min.) and excess diimine (t_ret 14.0 min.). The ice-cold reaction mixture is poured with stirring into 112 ml of ice/water under nitrogen, whereupon it becomes yellow in color and two phases form. It is extracted with 1×80 ml and 2×35 ml of dichloromethane. The combined extracts are concentrated in vacuo, and the residue is dried under HV. 13.2 g of yellow amorphous solid foam which, according to HPLC, comprises 45 area % imine-protected Mannich product, 7 area % pseudoephedrine amide (precursor) and diimine are obtained. This crude product is subjected to purification by chromatography with simultaneous elimination of the imine protective group. For this purpose, a glass column (diameter 7.0 cm, length 46 cm) is packed with 1770 ml (about 900 g) of silica gel 60 (Merck, 0.04-0.063 mm) in a Büchi medium-pressure system. The column is conditioned at a flow rate of 130 ml/min. with 1.5 l of CH₂Cl₂/MeOH/NH₄OH (25% strength) 9:1.5:0.3, then with 2 l of CH₂Cl₂. The crude product, dissolved in 15 ml of CH₂Cl₂, is then loaded onto the column. Nonpolar impurities are eluted with 1 l of CH₂Cl₂ followed by 0.5 l of CH₂Cl₂/MeOH 99:1, followed by 0.5 l of CH₂Cl₂/MeOH 98:2, followed by 0.5 l of CH₂Cl₂/MeOH 95:5. The product which undergoes aqueous deprotection on the column is then eluted with 1 l of CH₂Cl₂/MeOH/NH₄OH (25% strength) 9:0.5:0.1, followed by 3 l of CH₂Cl₂/MeOH/NH₄OH (25% strength) 9:1:0.2 followed by 2 l of CH₂Cl₂/MeOH/NH₄OH (25% strength) 9:1.5:0.3. Fractions of about 140 ml are taken (filling time 95 sec). Fractions 10-30 are combined with addition with toluene. Azeotropic entrainment of the water by toluene on concentration prevents the product remaining in residues of water from the ammonia, in which it would undergo a retro-Mannich reaction. The solvents are removed in vacuo, and the residue is dried under HV. 5.30 g of brown amorphous solid foam which has an HPLC purity of 97 area % are obtained.

Yield: 6.11 mmol, equivalent to 63% of theory.

¹H-NMR (400 MHz, CDCl₃): two sets of signals are present, because there are two rotamers (ratio about 3:1) of the amide function. Signals of the main rotamer are identified by (*), and signals of the subsidiary rotamer by (#). Unidentified signals are ascribed to overlapping rotamer signals. δ=0.64 (*), 0.72 (#) (2×d, 3H, C—CH₃); 1.30-1.68 (m, 5H, C<u>H</u>₂—CH₂—C<u>H</u>—C=O); 2.08 (s, very broad, 1H, OH); 2.14 (s, sharp, 2H, NH₂); 2.35 (*), 2.74 (#) (2×s, 3H, NCH₃); 2.72 (*), 2.81 (#) (2×m, 1H, C<u>H</u>—NHaryl); 3.59 (#), 3.66 (*) (2×s, 2H, C<u>H</u>₂NH₂); 3.71 (*), 3.74 (#) (2×s, 3H, OCH₃); 3.73 (#, mostly overlapped), 4.55 (*, qui) (1H, C<u>H</u>CH₃); 4.26 (#), 4.43 (*) (2×dd, 1H, C<u>H</u>Otrityl); 4.30 (d, 1H, N<u>H</u>aryl); 4.36 (t, 1H, C<u>H</u>OH); 6.34 (*), 6.35 (#) (2×d, 2H, arom.-H); 6.70-7.45 (m, 30H, arom.-H). HPLC-MS (Quattroultima, TOF, positive ESI): single peak, t_ret 21.82 min.), m/z=842 (8%, M+H⁺), 583 (98%, M+H⁺—Ph₃CO.), 243 (100%, Ph₃C⁺).

HPLC, HPLC-MS and ¹H-NMR of the Mannich product provide no evidence of a diastereomer present in a small amount. The stereoselectivity of the Mannich addition therefore appears to be high.

EXAMPLE 26

[2(S)-Hydroxy-1(S)-methyl-2-phenylethyl]-N-methyl-2(R)-[(4-aminomethyl-phenylamino)-(4-methoxyphenyl)-(S)-methyl]-5(S)-[(Ethoxymethoxy)-(4-fluorophenyl)]pentanamide] ("ethoxymethoxy-protected, imine-deprotected Mannich Product")

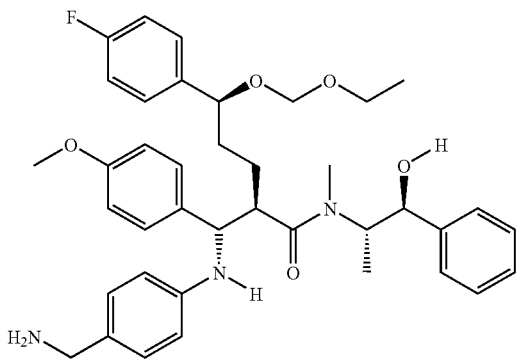

Lithium chloride (99% pure) is dried at 150-200° C./4×10⁻³ mbar for 3 h. Diisopropylamine (99.5% pure) is distilled fresh from $CaH_2$ and then contains 0.02% by weight water according to Karl-Fischer titration. Tetrahydrofuran (THF, Fluka) is degassed by bubbling through dried argon and contains <0.005% by weight water according to Karl-Fischer titration.

17.0 ml of THF and 4.44 ml (31.5 mmol) of diisopropylamine are added to 3.54 g (82.7 mmol) of dried lithium chloride in a thoroughly heat-dried four-neck round-bottom flask with magnetic stirrer, septum, argon inlet and low-temperature thermometer. The mixture is cooled to −78° C. in a dry ice/acetone bath, and 11.7 ml (29.3 mmol) of a 2.5 molar solution of n-butyllithium in hexane are added dropwise by syringe pump over the course of 20 min, during which a yellow coloration appears. The mixture is allowed to warm to 0° C. and is stirred at 0° C. for 5 min. It is again cooled to −78° C., and then a solution of 5.84 g (12.87 mmol) of the pseudoephedrine amide with a purity of 92 area % (from Example 23) in 28 ml of THF is added dropwise by syringe pump over the course of 20 min, during which the mixture becomes yellow in color. It is then stirred at −65° C. for 1 h. It is allowed to warm to 0° C. and is stirred at this temperature for 15 min and at room temperature for a further 5 min and is again cooled to 0° C. A solution of 10.0 g (27.9 mmol, 2 equivalents based on amide) of the bisimine (from Example 4) in 33 ml of THF is added dropwise over the course of 5 min, during which the reaction mixture becomes orange-red in color. It is stirred at 0° C. for 2.5 hours. HPLC monitoring of the course of the reaction (system as in Example 5) shows after 2 hours the imine-protected Mannich product (40 area %, $t_{ret}$ 16.0 min.) in addition to unreacted precursor (4.8 area %; $t_{ret}$ 12.7 min.) and excess diimine ($t_{ret}$ 13.9 min.). The ice-cold reaction mixture is poured with stirring into 156 ml of ice/water under nitrogen, whereupon it becomes yellow in color and two phases form. It is extracted with 1×110 ml and 2×50 ml of dichloromethane. The combined extracts are concentrated in vacuo, and the residue is dried under HV. 16.2 g of brown amorphous solid foam are obtained. This crude product is subjected to purification by chromatography with simultaneous elimination of the imine protective group. For this purpose, a glass column (diameter 7.0 cm, length 46 cm) is packed with 1770 ml (about 900 g) of silica gel 60 (Merck, 0.04-0.063 mm) in a Büchi medium-pressure system. The column is conditioned at a flow rate of 130 ml/min. with 3 l of $CH_2Cl_2$/MeOH/$NH_4OH$ (25% strength) 9:1.5:0.3, then with 2 l of $CH_2Cl_2$. The crude product, dissolved in 30 ml of $CH_2Cl_2$, is then loaded onto the column. Nonpolar impurities are eluted with 1 l of $CH_2Cl_2$ followed by 0.5 l of $CH_2Cl_2$/MeOH 99:1, followed by 0.5 l of $CH_2Cl_2$/MeOH 98:2, followed by 0.5 l of $CH_2Cl_2$/MeOH 95:5. The product which undergoes aqueous deprotection on the column is then eluted with 1 l of $CH_2Cl_2$/MeOH/$NH_4OH$ (25% strength) 9:0.5:0.1, followed by 4 l of $CH_2Cl_2$/MeOH/$NH_4OH$ (25% strength) 9:1:0.2 followed by 1 l of $CH_2Cl_2$/MeOH/$NH_4OH$ (25% strength) 9:1.5:0.3. Fractions of about 140 ml are taken (filling time 95 sec). Toward the end of the chromatography, the volume of the fractions become smaller because the pressure falls. Two diastereomers (213 mg, beige amorphous solid foam) of the main Mannich product are obtained in almost pure form in fraction 10. Fractions 13-24, which contain pure main Mannich product, are combined with addition of toluene. Azeotropic entrainment of the water by toluene on concentration prevents the product remaining in residues of water from the ammonia, in which it would undergo a retro-Mannich reaction. The solvents were removed in vacuo, and the residue was dried under HV. 5.56 g of pale brown amorphous solid foam which has an HPLC purity of 99 area % are obtained. Yield: 8.37 mmol, equivalent to 65% of theory.

¹H-NMR (400 MHz, $CDCl_3$): two sets of signals are present because there are two rotamers (ratio about 3.5:1) of the amide function. Signals of the main rotamer are identified by (*), and signals of the subsidiary rotamer by (#). Unidentified signals are ascribed to overlapping rotamer signals. δ=0.67 (*), 0.81 (#) (2×d, 3H, C—C$\underline{H}_3$); 1.08 (#), 1.10 (*) (2×t, 3H, OCH$_2$C$\underline{H}_3$); 1.50-2.14 (m, 5H, C$\underline{H}_2$—C$\underline{H}_2$—C$\underline{H}$—C═O); 2.31 (*), 2.83 (#) (2×s, 3H, NCH$_3$); 3.16 (*), 3.45 (#) (2×dqua, 1H, NC$\underline{H}$—CH$_3$); 3.27 (#), 3.41 (*) (2×dd, 1H, C$\underline{H}$NHaryl); 3.57 (#), 3.63 (*) (2×s, broadened, 2H, C$\underline{H}_2$NH$_2$); 3.72 (*), 3.76 (#) (2×s, 3H, OCH$_3$); 4.15 (#), 4.74 (*) (2×~qui broad, 1H, C$\underline{H}$OH); 4.36 (dd, 1H, C$\underline{H}$OCH$_2$O); 4.44 (#), 4.52 (*) (2×qua, 2H, C$\underline{H}_2$CH$_3$); 4.48 (d, 1H, OC$\underline{H}$O); 4.58 (d, 1H, OC$\underline{H}$O); 5.97 (d, broadened, 1H, aryl-N$\underline{H}$); 6.42 (*), 6.44 (#) (2×d, 2H, arom.-H); 6.63-7.43 (m, 15H, arom.-H). HPLC-MS (Quattroultima, TOF, positive ESI): single peak, $t_{ret}$ 13.30 min.), m/z=658 (100%, M+H⁺), 641 (32%, M+H⁺—NH$_3$), 536 (32%, M+H⁺—H$_2$NCH$_2$—C$_6$H$_4$—NH$_2$).

HPLC, HPLC-MS and ¹H-NMR of the Mannich product provide no evidence of a diastereomer present in a small amount. Stereoisomers are present only in pre-fraction 10 (231 mg). The stereoselectivity of the Mannich addition is therefore high (total of diastereomers about 4%).

EXAMPLE 27

2(R)-[(4-Aminomethylphenylamino)-(4-methoxyphenyl)-(S)-methyl]-5-(4-fluorophenyl)-5(S)-[tetrahydropyran-2(RS)-yloxy]pentanoic acid

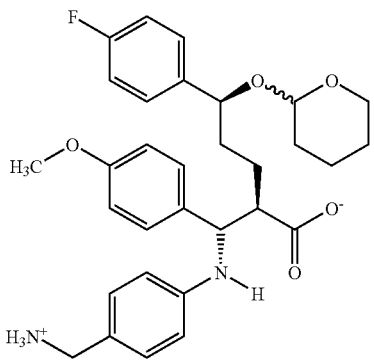

A clear yellow solution of 2.07 g (3.00 mmol) of THP-protected, imine-deprotected Mannich product with a purity of >99 area % (from Example 24) in 15 ml of ethanol is heated to 75° C. in a three-neck flask with stirring bar and reflux condenser under nitrogen, and 10.0 ml (32.2 mmol) of 3.22 N aqueous sodium hydroxide solution are slowly added dropwise. The mixture is then heated to reflux for 6 days while keeping the volume constant (occasional addition of ethanol to compensate for evaporation losses). HPLC monitoring (system as in Example 5, det. 254 nm) shows 95% conversion to four isomeric products (peak area ratio 17.8:12.5:38.8:30.8; $t_{ret}$ 8.36, 8.40, 8.53 and 8.63 min.) and (analysis at 210 nm) eliminated pseudoephedrine at $t_{ret}$ 4.4 min. The reaction mixture is cooled, 20 ml of water are added, and the mixture is then concentrated in vacuo to a total volume of about 20 ml in order to remove the ethanol. A further 20 ml of water are added to the aqueous residue, and it is again concentrated. The crystallized solid is redissolved by adding 20 ml of water. The aqueous solution is washed with 2×20 ml of diethyl ether. The aqueous solution is cooled in an ice bath and the pH is adjusted, starting from pH 13.2, to 7.5 by slow dropwise addition of 14.4 ml of 2N aqueous hydrochloric acid while monitoring with a pH electrode, whereupon an increasingly dense solid mass precipitates. It is filtered off with suction, washed with water and dried over phosphorus pentoxide under HV. This crude product (2.57 g, 160% of theory) contains silicates produced through the action of the hot sodium hydroxide solution on the wall of the flask. The crude product is mixed with 125 ml of ethanol, and the suspension is stirred at room temperature for 2 hours. The undissolved residue is filtered off with suction using a glass frit and washed several times with ethanol. The filtrate is concentrated in vacuo and the residue is dried under HV. 1.11 g (2.07 mmol, 69% of theory) of beige amorphous solid foam which has an HPLC purity of 99 area % and which comprises the four diastereomers in the ratio 18:13:38:31, virtually unchanged from the isomeric composition of the reaction mixture which has reacted, are obtained. Thus, the stereocenter α to the carbonyl group epimerizes in about 31% of the precursor. The desired product and its epimer are both in the form of an approximately 1.3:1 mixture of diastereomers owing to the stereocenter in the THP protective group.

$^1$H-NMR (400 MHz, DMSO-$d_6$): δ=1.20-1.84 (m, 10H, 5×CH$_2$), 2.26-2.46 (m, 1H, CHCO$_2$), 3.17 (m, 1H, OCH$_2$CH$_2$), 3.38 (m, 1H, OCH$_2$CH$_2$), 3.58 (s slightly broadened, 2H, CH$_2$N), 3.68 (s, 3H, OCH$_3$), 4.17-4.63 (m, 4H, CHN Haryl, arylCHOCHO—), 6.32 (m, 2H, arom.-H), 6.75 (dt, 2H, arom.-H), 6.95 (m, 2H, arom.-H), 7.07 (dt, 2H, arom.-H), 7.13-7.32 (m, 4H, arom.-H). HPLC-MS (Quattroultima, TOF, positive ESI): all 4 isomers ($t_{ret}$=11.60, 11.91, 12.16 and 12.55 min.) show m/z=537 (3-10%, M+H$^+$), 520 (100%, M+H$^+$—NH$_3$).

EXAMPLE 28

2(R)-[(4-Aminomethylphenylamino)-(4-methoxyphenyl)-(S)-methyl]-5-(4-fluorophenyl)-5(S)-(trityloxy)pentanoic acid

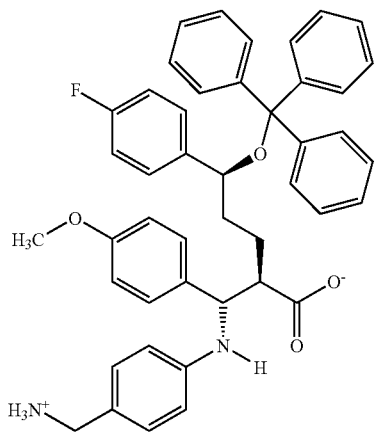

A clear yellow solution of 2.19 g (2.52 mmol) of trityl-protected, imine-deprotected Mannich product with a purity of 97 area % (from Example 25) in 15 ml of ethanol is heated to 75° C. in a three-neck flask with stirring bar and reflux condenser under nitrogen, and 9.0 ml (29.0 mmol) of 3.22 N aqueous sodium hydroxide solution are slowly added dropwise. The brown cloudy solution is then heated to reflux while stirring vigorously and keeping the volume constant (occasional addition of ethanol to compensate for evaporation losses) for 7 days. HPLC monitoring (system as in Example 5, det. 254 nm) shows 92% conversion to two isomeric products (peak area ratio 40:60; $t_{ret}$ 12.1 and 12.2 min.) and (analysis at 210 nm) eliminated pseudoephedrine ($t_{ret}$ 4.4 min.). The reaction mixture is cooled, 20 ml of water are added, and then the mixture is concentrated in vacuo to a total volume of about 20 ml in order to remove the ethanol. A further 20 ml of water are added to the aqueous residue, and it is again evaporated. 20 ml of water are added. The resulting emulsion is washed with 2×20 ml of diethyl ether. The aqueous phase is cooled in an ice bath and the pH is adjusted, starting from pH 13.2, to 7.5 by slow dropwise addition of 12.5 ml of 2N aqueous hydrochloric acid while monitoring with a pH electrode, during which an increasingly dense solid mass precipitates. It is filtered off with suction, washed with water and dried over phosphorus pentoxide under HV. This crude product (2.38 g, 136% of theory) contains silicates produced by the action of the hot sodium hydroxide solution on the wall of the flask. The crude product is mixed with 125 ml of ethanol, and the suspension is stirred at room temperature for 2 hours. The undissolved residue is filtered off with suction using a glass frit and washed several times with ethanol. The filtrate is concentrated in vacuo, and the residue is dried under HV. 1.48 g (2.13 mmol, 84% of theory) of beige amorphous solid foam which has an HPLC purity of 95 area % and comprises two diastereomers in the ratio 38:62 are obtained. The 38% diastereomer are produced by epimerization of the stereocenter α to the carbonyl group during the amide cleavage.

$^1$H-NMR (400 MHz, DMSO-$d_6$): δ=1.10-1.36 (m, 2H, $CH_2$), 1.48-1.65 (m, 2H, $CH_2$), 2.05 (m, 1H, $CHCO_2$), 3.55 (s, broad, 3H, $NH_3^+$), 3.62 (s, 2H, $CH_2N$), 3.68 (s, 3H, $OCH_3$), 4.03 (d, 1H, NH), 4.25 (m, 1H, CHN), 4.44 (~t, 1H, CHOCPh$_3$), 6.24 (m, 2H, arom.-H), 6.64 and 6.70 (2×d, 2H, arom.-H), 6.73-7.10 (m, 8H, arom.-H), 7.10-7.25 (m, 9H, arom.-H), 7.25-7.37 (m, 6H, arom.-H). HPLC-MS (Quattroultima, TOF, positive ESI): both diastereomers ($t_{ret}$=15.54 and 16.18 min.) show m/z=694 (respectively 4 and 12%, $M^+$), 678 (respectively 94 and 81%, $M+H^+$—$NH_3$), 436 (100%, $M+H^+$—$Ph_3CO$.), 243 (respectively 87 and 72%, $Ph_3C^+$).

EXAMPLE 29

2(R)-[(4-Aminomethylphenylamino)-(4-methoxyphenyl)-(S)-methyl]-5(S)-(ethoxymethoxy)-5-(4-fluorophenyl)pentanoic acid

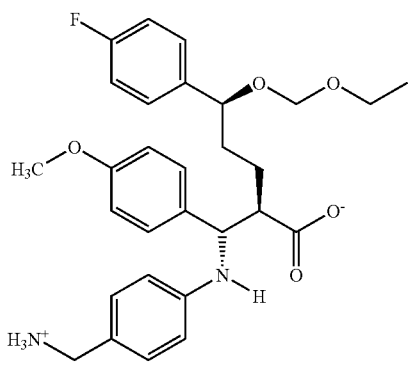

A clear yellow solution of 1.99 g (3.00 mmol) of ethoxymethoxy-protected, imine-deprotected Mannich product with a purity of >99 area % (from Example 26) in 15 ml of ethanol is heated to 75° C. in a three-neck flask with stirring bar and reflux condenser under nitrogen, and 10.0 ml (32.2 mmol) of 3.22 N aqueous sodium hydroxide solution are slowly added dropwise. The pale yellow clear solution is then heated to reflux while stirring vigorously and keeping the volume constant (occasional addition of ethanol to compensate for evaporation losses) for 4 days. HPLC monitoring (system as in Example 5, det. 254 nm) shows 94% conversion to two isomeric products (peak area ratio 31:69; $t_{ret}$ 8.0 and 8.2 min.) and (analysis at 210 nm) eliminated pseudoephedrine ($t_{ret}$ 4.4 min.). The reaction mixture is cooled, 20 ml of water are added, and then the mixture is concentrated to a total volume of about 20 ml in vacuo in order to remove the ethanol. A further 20 ml of water are added to the aqueous residue, and it is again concentrated. 20 ml of water are added, and washed with 2×20 ml of diethyl ether. The aqueous phase is filtered through a glass frit in order to remove insolubles. The filtrate is cooled in an ice bath and the pH is adjusted, starting from pH 13.3 to 7.5 by slow dropwise addition of 13.4 ml of 2N aqueous hydrochloric acid while monitoring with a pH electrode, whereupon an increasingly dense yellow solid mass precipitates. It is filtered off with suction, washed with water and dried over phosphorus pentoxide under HV. This crude product (2.25 g, 146% of theory) contains silicates produced by the action of the hot sodium hydroxide solution on the wall of the flask. The crude product is mixed with 125 ml of ethanol and the suspension is stirred at room temperature for 2 hours. The undissolved colorless residue is filtered off with suction using a glass frit and washed several times with ethanol. The filtrate is concentrated in vacuo and the residue is dried under HV. 1.33 g (2.60 mmol, 87% of theory) of beige amorphous solid foam which has an HPLC purity of 99 area % and comprises two diastereomers in the ratio 33:67 are obtained. The 33% diastereomer are produced by epimerization of the stereocenter α to the carbonyl group during the amide cleavage. The "wrong" diastereomer (epimerization product) is greatly enriched in the aqueous mother liquor of the precipitation of the reaction product (by neutralization). This indicates a satisfactory possibility for purifying the desired diastereomer by recrystallization from hot water.

$^1$H-NMR (400 MHz, DMSO-$d_6$): δ=1.01 (t, 3H, $CH_3CH_2O$), 1.17 (m, 1H, $CH_2$), 1.40 (m, 1H, $CH_2$), 1.50-1.86 (m, 2H, $CH_2$), 2.30-2.46 (m, 1H, $CHCO_2$), 3.21-3.37 (m, 1H, $CH_3CH_2O$), 3.38-3.54 (m, 1H, $CH_3CH_2O$), 3.59 and 3.61 (2×s, slightly broadened, 2H, $CH_2N$), 3.69 (s, 3H, $OCH_3$), 4.19 (d, slightly broadened, 1H, NH), NCH), 4.29 (d, 1H, OCH$_2$O), 4.32-4.43 (m, 1H, CHNHaryl), 4.45 (d, 1H, OCH$_2$O), 4.47 (m, partly concealed, 1H, CHOCH$_2$O), 6.28 and 6.32 (2×d, 2H, arom.-H), 6.73 and 6.74 (2×d, 2H, arom.-H), 6.96 and 6.98 (2×d, 2H, arom.-H), 7.04-7.28 (m, 6H, arom.-H). HPLC-MS (Quattroultima, TOF, positive ESI): both diastereomers ($t_{ret}$=10.83 and 11.39 min.) show m/z=511 (respectively 1 and 2%, $M+H^+$), 494(100%, $M+H^+$—$NH_3$).

EXAMPLE 30

[2(S)-Hydroxy-1(S)-methyl-2-phenylethyl]-N-methyl-2(R)-[(4-aminomethylphenylamino)-(4-methoxyphenyl)-(S)-methyl]-5(S)-[(4-fluorophenyl)-5-hydroxyl]pentanamide] ("hydroxyl-unprotected, Imine-deprotected Mannich Product")

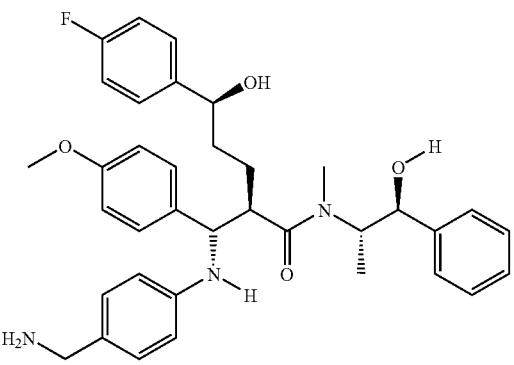

14 mg (0.058 mmol, 5 mol equiv.) of pyridinium p-toluenesulfonate and 111 mg (0.58 mmol, 50 mol equiv.) of p-toluenesulfonic acid hydrate are added to a solution of 800 mg (1.16 mmol) of THP-protected, imine-deprotected Mannich product with a purity of 99 area % (from Example 24) in 20 ml of methanol in a one-neck round-bottom flask. After the solution has been stored overnight, HPLC (system as in Example 5; det. 254 nm) shows only slight THP elimination from the precursor ($t_{ret}$ 13.2 min.) to form the product ($t_{ret}$ 10.3 min.). A further 111 mg (0.58 mmol, 50 mol-equiv.) of p-toluenesulfonic acid hydrate are added. HPLC monitoring shows a clean course of the reaction with 25% THP elimination after 1 hour, 44% after 4 hours and 83% after 20 hours. 20 ml of p-xylene (b.p. 138° C.) are added to the reaction mixture, and then the solvents and the 2-methoxy-THP (Lit. b.p. 128-129° C.) which has formed are distilled off in vacuo, finally at 40° C., 6 mbar). The solid residue is taken up in 20 ml in p-xylene, and the solvent is again distilled off in vacuo. The yellowish solid is dissolved in 20 ml of methanol and left to stand in a closed flask at room temperature for 16 hours. HPLC shows 93.0 area % of the product and 5.4 area % of the precursor. 20 ml of p-xylene are added, and then the solvents and any 2-methoxy-THP formed are distilled off in vacuo. The yellowish solid is dissolved in 30 ml of dichloromethane and washed with 2×10 ml of saturated aqueous $NaHCO_3$ solution and with 10 ml of water. The dichloromethane is distilled off in vacuo and the residue is dried under HV. 649 mg (1.082 mmol, 93% of theory) of pale beige crystalline solid which, according to HPLC, comprises 95 area % of the product (about 616 mg, 1.027 mmol, 89% of theory) and 5 area % of the precursor is obtained. $^1$H-NMR (400 MHz, $CDCl_3$): the product shows two sets of signals owing to the presence of 2 rotamers (ratio about 5:1). Signals of the main rotamer are identified by (*), and signals of the subsidiary rotamer by (#). Unidentified signals are ascribed to overlapping rotamer signals. δ=0.66 (*), 0.82 (#) (2×d, C—$CH_3$); 1.56-1.89 (m, 4H, 2×$CH_2$); 2.18 (m, 1H, C$\underline{H}$—C=O); 2.28 (*), 2.82 (#) (2×s, 3H, N—$CH_3$); 2.31 (s, 2H, $NH_2$); 3.24 (*), 3.32 (#) (2×m, 1H, NC$\underline{H}$—$CH_3$); 3.55 (#), 3.59 (*) (2×s, slightly broadened, 2H, C$\underline{H_2}NH_2$); 3.72 (*), 3.74 (#) (2×s, 3H, $OCH_3$); 4.12 (#), 4.83 (*) (2×qui, 1H, $CH_2C\underline{H}OH$); 4.34 (*), 4.42 (#) (2×d, 1H, OH); 4.47 (#), 4.61 (*) (2×dd, 1H, CHMe-C$\underline{H}$OH); 4.52 (*), 4.56 (#) (2×dd, 1H, C$\underline{H}$NHaryl); 5.98 (d, slightly broadened, 1H, NH); 6.42 (*), 6.44 (#) (2×d, 2H, arom.-H); 6.77 (d, 2H, arom.-H); 6.83-7.41 (m, 13H, arom.-H). FT-IR (solid): ν=3355 (broad, stretching vibration of O—H, N—H, $NH_2$), 1613 (C=O stretching vibration of the amide), 1576 (arC–C), 1246, 1217, 1027, 835, 702 cm$^{-1}$.

HPLC-MS (Quattroultima, TOF, positive ESI): product ($t_{ret}$=10.00 min.) shows m/z=600 (100%, M+H$^+$), 583 (92%, M+H$^+$—$NH_3$); precursor ($t_{ret}$=12.66 min.) shows m/z=684 (65%, M+H$^+$), 667 (100%, M+H$^+$—$NH_3$).

EXAMPLE 31

2(R)-[(4-Aminomethylphenylamino)-(4-methoxyphenyl)-(S)-methyl]-5-(4-fluorophenyl)-5(S)-hydroxypentanoic Acid

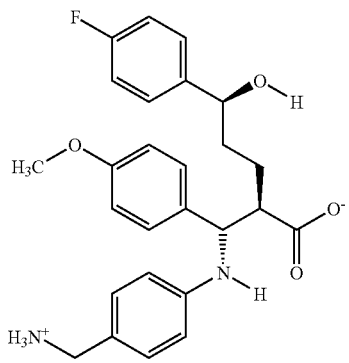

To 360 mg (0.60 mmol) of the hydroxy-unprotected, imine-deprotected Mannich product (from Example 30) in a three-neck pear-shaped flask with stirring bar are added 5 ml of ethanol and then, just below the boiling point, 5 ml (16.2 mmol, 27 equivalents) of 3.22 N aqueous sodium hydroxide solution. The clear yellowish solution is heated to reflux. An HPLC check (system as in Example 5, det. 254 nm) after 3 h shows no remaining precursor ($t_{ret}$ 10.5 min.), 82 area % of the expected carboxylic acid ($t_{ret}$ 6.9 min.), 14 area % of the epimeric carboxylic acid ($t_{ret}$ 6.5 min.) and 4 area % of an impurity ($t_{ret}$ 13.8 min.). Eliminated pseudoephedrine is identifiable at 210 nm ($t_{ret}$ 4.4 min.). The cooled solution of the mixture is mixed with 11 ml of deionized water and concentrated in vacuo in order to remove ethanol. A further 11 ml of deionized water are added and again concentrated in vacuo. The oily residue is dissolved by adding deionized water, and the basic solution is then washed with 2×11 ml of diethyl ether. HPLC of the ether phases shows pseudoephedrine and no more than slight traces of the product. HPLC of the aqueous phase shows the desired carboxylic acid and its epimer in the ratio 87:13 with a purity of 99.5 area %. The aqueous phase is adjusted from pH 14.1 to pH 7 to 8 with about 8 ml of 2N hydrochloric acid while cooling in an ice bath (monitoring with a glass electrode), an oil separating out from about pH 11 onward, and crystallizing on addition of a seed crystal. The precipitate is then stirred in the ice bath for 30 min, filtered off with suction, washed with water and dried over Sicapent under high vacuum. 173 mg (0.38 mmol, 64% of theory) of beige solid which has an HPLC purity of >99 area % and comprises the desired carboxylic acid and its epimer in the ratio 92:8 are obtained. $^1$H-NMR and MS data of the product correspond to those of the product from Example 10.

The epimer is enriched to 30 area % in the aqueous mother liquor.

EXAMPLE 32

Methyl 5-(4-fluorophenyl)-5(S)-hydroxypentanoate by Asymmetric Hydrosilylation With a Substrate to Ligand Ratio of 200:1

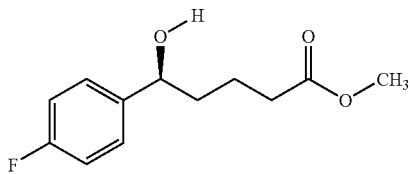

Commercial sodium tert-butoxide is sublimed under high vacuum and stored in a desiccator under argon until used shortly thereafter. The toluene employed is degassed over predried molecular sieves (0.4 nm) in an ultrasonic bath for 5 min. Glass flasks are dried with hot air in a stream of argon. The solids are weighed out under a gentle countercurrent of argon. Solvents are added and samples are taken through a septum in the flask using syringes/needles which are stored over phosphorus pentoxide in a desiccator until used.

25.8 mg (0.26 mmol) of copper(I) chloride, 25.6 mg (0.26 mmol) of sodium tert-butoxide and 27.4 mg (0.0436 mmol) of (R)-(+)-BINAP are weighed into a 25 ml three-neck sulfonation flask with stirring bar, septum, thermosensor and stopper. The flask is cooled to −50° C. under argon using a cooling bath (isopropanol/dry ice). 12.5 ml of degassed toluene are added with a needle through the septum. After stirring at −50° C. for 15 min, the mixture is warmed to 0° C. by replacing the cooling bath by an ice bath, stirred for about 2 min, and then cooled to −50° C. again. This procedure is repeated three times. An almost clear solution is produced thereby. In a separate sulfonation flask, a solution of 1.97 g (8.70 mmol) of 99% pure methyl 5-(4-fluorophenyl)-5-oxopentanoate in 5 ml of degassed toluene is prepared (solubility about 630 mg/ml). 2.8 ml (46.8 mmol, 5.38 equivalents based on the keto ester) of poly(methylhydrosiloxane) (PMHS) are slowly added dropwise to the catalyst solution at −50° C. The mixture is warmed to 0° C. with an ice bath and the toluene solution of the keto ester is added dropwise over the course of 10 min. The yellow reaction solution is then immediately cooled to −10° C. and stirred further at this temperature. An HPLC sample taken after a reaction time of 30 min (i.e. 20 min after the end of addition) shows 77% clean conversion of the precursor to the alcohol. The conversion after a reaction time of 1 hour is 97%, and less than 0.4 area % precursor and 96 area % of the alcohol are detected after 2 hours. The reaction mixture is poured into 200 ml of ice-cold 1% strength acetic acid (glass beaker) and vigorously stirred for 30 min. 50 ml of toluene are added, the ice bath is removed, and vigorous stirring is continued at about 20° C. for 1 hour. The clear colorless aqueous phase (lower) is separated off and the pale yellow cloudy organic phase (upper) is again vigorously stirred with 50 ml of 1% strength aqueous acetic acid for 1 hour. The aqueous phase is separated off and the organic phase is dried over sodium sulfate. Filtration and concentration of the organic phase in vacuo, followed by drying of the residue under high vacuum, affords 1.97 g (100% of theory) of yellowish oil. $^1$H-NMR corresponds to that of the product from Example 1. Chiral phase HPLC (system as in Example 1) afforded 93% ee of the desired (S) alcohol.

EXAMPLE 33

Methyl 5-(4-fluorophenyl)-5(S)-hydroxypentanoate by Asymmetric Hydrosilylation With a Substrate to Ligand Ratio of 3660:1

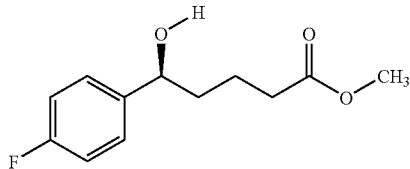

Commercial sodium tert-butoxide is sublimed under high vacuum and stored in a desiccator under argon until used shortly thereafter. The toluene employed is degassed over predried molecular sieves (0.4 nm) in an ultrasonic bath for 5 min. Glass flasks are dried with hot air in a stream of argon. The solids are weighed out under a gentle countercurrent of argon. Solvents are added and samples are taken through a septum in the flask using syringes/needles which are stored over phosphorus pentoxide in a desiccator until used.

25.5 mg (0.258 mmol) of copper(I) chloride and 25.3 mg (0.258 mmol) of sodium tert-butoxide are weighed into a 25 ml three-neck sulfonation flask with stirring bar, septum, thermosensor and stopper. The flask is cooled to −10° C. and 12.5 ml of degassed toluene are added by needle through the septum. After stirring at −10° C. for 15 minutes, the mixture is warmed to 0° C., stirred for 2 min and again cooled to −10° C. 1.50 mg (0.0024 mmol) of (R)-(+)-BINAP as solution in toluene (3.12 ml of a solution with a concentration of 0.48 mg/ml) are added through the septum, and the mixture is again warmed to 0° C. for 2 min and cooled again to −10° C., resulting in an almost clear solution. In a separate sulfonation flask, a solution of 1.97 g (8.70 mmol) of 99% pure methyl 5-(4-fluorophenyl)-5-oxopentanoate in 5 ml of degassed toluene is prepared (solubility about 630 mg/ml). 2.8 ml (46.8 mmol, 5.38 equivalents based on the keto ester) of poly(m-ethylhydrosiloxane) are slowly added dropwise by syringe to the catalyst solution at −10° C. Immediately thereafter, at −10° C., the toluene solution of precursor is added dropwise by syringe over the course of 5 min. The mixture is then stirred at −10° C. under an argon atmosphere for 12 h. A sample shows 97% clean conversion of the precursor in the alcohol and only 0.9 area % of precursor in the HPLC. The reaction mixture is poured through a fluted filter onto 100 ml of ice-cold 1% strength acetic acid (glass beaker) and vigorously stirred for 1 h. The clear colorless aqueous phase (lower) is separated off and the beige-colored milky-turbid organic phase (upper) is again stirred vigorously with 50 ml of 1% strength aqueous acetic acid for 1 hour. The aqueous phase is separated off and the organic phase is dried over sodium sulfate. Filtration and concentration of the organic phase in vacuo, followed by drying of the residue under high vacuum, affords 1.96 g (100% of theory) of yellowish brown oil. $^1$H-NMR corresponds to that of the product from Example 1. Chiral phase HPLC (system as in Example 1) affords 90% ee of the desired (S) alcohol.

EXAMPLE 34

[2-(S)-Hydroxy-1(S)-methyl-2-phenylethy]-N-methyl-5-(4-fluorophenyl)-5-oxopentanamide

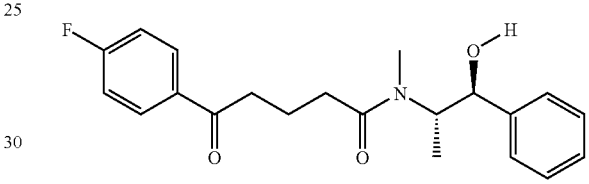

Firstly 30.4 g (0.3 mol, 1.5 mol equivalents) of triethylamine and then slowly 21.7 g (0.2 mol, 1.0 mol equivalent) are added dropwise to a solution of 42.0 g (0.2 mol) of 5-(4-fluorophenyl)-5-oxopentanoic acid in 500 ml of anhydrous tetrahydrofuran at 0-5° C. The mixture is then stirred at 0-5° C. for one hour. 33.0 g (0.2 mol, 1.0 mol equivalent) of (+)-(1S,2S)-pseudoephedrine are then introduced in portions. The reaction is completed by stirring at 20-25° C. for two hours (TLC check: dichloromethane/methanol=9/1). The solvent is substantially distilled off in vacuo and 200 ml of ice-water are added to the residue. The product is extracted with ethyl acetate (2×250 ml), and the organic phase is washed successively with 100 ml each of 2N hydrochloric acid, saturated sodium bicarbonate solution and saturated sodium chloride solution. The solution is dried over sodium sulfate, filtered and concentrated in vacuo. 61.9 g (173 mmol, 86% of theory) of an oil which crystallizes after some days are obtained (m.p.: 87-88° C.).

HPLC-MS [column: 20×2 mm YMC J'sphere ODS H 80; eluent: A: 0.5% trifluoroacetic acid in water, eluent B: 0.5% trifluoroacetic acid in acetonitrile, gradient: T=0 min.: 96% A, T=2 min.: 95% B, T=2.4 min.: 95% B, flow rate: 1 ml/min.; temp.: 30° C.; UV detection at 220 nm, $t_{ret}$ 1.33 min.] results in a purity (area percent) of 94% (m/z=358 (100%, M+H$^+$).

$^1$H-NMR (400 MHz, CDCl$_3$): two sets of signals owing to the presence of two rotamers (ratio about 1.6:1) of the amide function. Signals of the main rotamer are identified by (*), and signals of the subsidiary rotamer by (#). Unidentified signals are ascribed to overlapping rotamer signals. δ=0.98 (#), 1.10 (*) (2×d, C—CH$_3$); 2.0-2.15 and 2.33-2.52 (2×m, 4H, 2×CH$_2$); 2.85 (#), 2.92 (*) (2×s, 3H, N—CH$_3$); 2.99-3.13 (m, 2H, CH$_2$); 4.11 (m, 1H, NCH—CH$_3$); 4.48 (m, broad, 1H, OH); 4.58 (m, 1H, CH$_2$CHOH); 7.09-7.42 (m, 7H, arom.-H); 7.96-8.09 (m, 2H, arom.-H).

EXAMPLE 35

4-[2-(4-Fluorophenyl)-[1,3]dioxolan-2-yl]-N)((S)-2-hydroxy-(S)-1-methyl-2-phenylethyl)-N-methylbutyramide

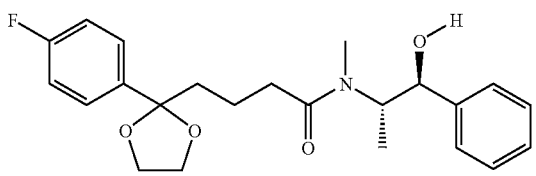

10.2 ml (180 mmol, 6 mol equivalents) of ethylene glycol and 570 mg (3 mmol, 0.1 mol equivalent) of p-toluenesulfonic acid monohydrate are added to a suspension of 10.7 g (30 mmol) of [2-(S)-hydroxy-1(S)-methyl-2-phenylethy]-N-methyl-5-(4-fluorophenyl)-5-oxopentanamide in 100 ml of toluene. The mixture is then heated under reflux with a water trap for 9 h. The cold reaction solution is washed with 50 ml of saturated sodium bicarbonate solution, dried over sodium sulfate, filtered and concentrated in vacuo. The residue is purified by chromatography (200 g of silica gel 35-70 μm, mobile phase: n-heptane/ethyl acetate=1/1, then ethyl acetate). 3.3 g (8.2 mmol, 27% of theory) of an oil are obtained.

HPLC-MS [column: 20×2 mm YMC J'sphere ODS H 80; eluent: A: 0.5% trifluoroacetic acid in water, eluent B: 0.5% trifluoroacetic acid in acetonitrile, gradient: T=0 min.: 96% A, T=2 min.: 95% B, T=2.4 Min.: 95% B, flow rate: 1 ml/min.; temp.: 30° C.; UV detection at 220 nm, $t_{ret}$ 1.27 min.] results in a purity (area percent) of 95% (m/z=402 (100%, M+H$^+$).

$^1$H-NMR (400 MHz, CDCl$_3$): two sets of signals owing to the presence of two rotamers (ratio about 2:1) of the amide function. Signals of the main rotamer are identified by (*), and signals of the subsidiary rotamer by (#).

Unidentified signals are ascribed to overlapping rotamer signals. δ=1.25 (*), 1.38 (#) (2×d, C—CH$_3$); 1.74-2.03 and (m, 4H, 2×CH$_2$); 2.81 (*), 2.86 (#) (2×s, 3H, N—CH$_3$); 2.74-2.95 (m, 2H, CH$_2$); 3.55-3.74 (2m, 4H, CH$_2$); (3.95-4.10 (m, 1H, NCH—CH$_3$); 4.73 (m, 1H, CH$_2$CHOH); 7.08-7.35 (m, 7H, arom.-H); 7.94-8.03 (m, 2H, arom.-H).

REFERENCE EXAMPLE C1

3(R)-[3(S)-(tert-Butyldimethylsilanoyloxy)-3-(4-fluorophenyl)propyl]-1-(4-{[(4-methoxybenzylidene)amino]methyl}phenyl)-4(S)-(4-methoxyphenyl)-azetidin-2-one

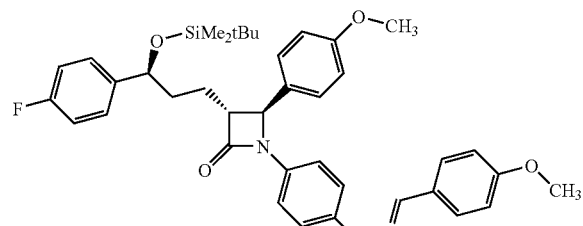

Preparation of a reference sample of the imine-protected β-lactam from an authentic sample of the free amino β-lactam.

Authentic 1-(4-aminomethylphenyl)-3(R)-[3(S)-(tert-butyldimethyl-silanyloxy)-3-(4-fluorophenyl)propyl]-4(S)-(4-methoxyphenyl)azetidin-2-one is prepared as described in WO 02/50027.

200 μl (1.61 mmol) of p-anisaldehyde (Fluka) are added to a solution of 827 mg (1.45 mmol) of 96% pure authentic amino β-lactam in 6 ml of toluene in a round-bottom flask with magnetic stirrer, distillation apparatus, dropping funnel and thermometer under nitrogen. The reaction mixture is heated to 50° C. in an oil bath. Even during the heating up, condensate is deposited on the wall of the flask. The pressure is reduced to 90 mbar so that toluene continuously distills out and is replaced by dropwise addition of toluene from the dropping funnel. An HPLC check shows virtually quantitative conversion after 15 min. The reaction mixture is concentrated in vacuo, and remaining toluene is removed under HV. Yield: 980 mg (1.47 mmol, 100% of theory) of viscous yellowish oil.

$^1$H-NMR, MS and HPLC retention time are identical to that of the product from Example 15.

What is claimed is:

1. A process for the preparing of diphenylazetidinone derivative of formula (I),

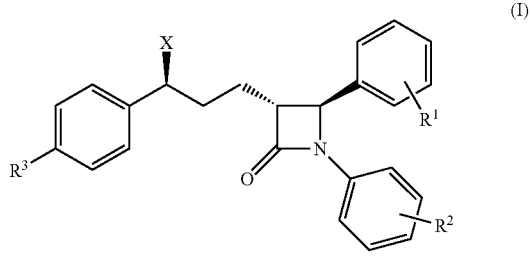

wherein:
X is OH;
R$^1$ is OH, or OCH$_3$;
R$^2$ is F, CH$_2$CH$_3$, or CH$_2$NHR$^4$;
R$^3$ is H, or F;
R$^4$ is H, CO—(CH$_2$—)$_n$CO—R$^5$, or CO—(CH$_2$—)$_n$NHR$^6$;
n is an integers from 4 to 16;
R$^5$ is OH or NH—CH$_2$—[CH(OH)—]$_m$CH$_2$OH;
R$^6$ is H or CO—[CH(OH)—]$_m$CH$_2$OH; and
m is an integers from 1 to 5;
comprising
(a) reacting a compound of formula (II)

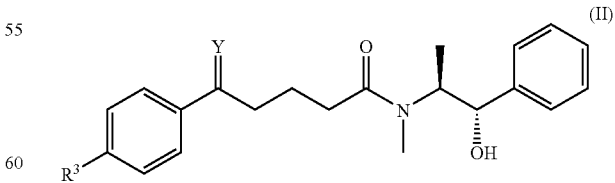

wherein:
Y is H, OH; H, O-acetyl; H, OSi(alkyl)$_o$(aryl)$_p$ wherein o and p are independently 0, 1, 2 or 3, and o+p is 3; H, O-tetrahydropyranyl; H, OC(aryl)$_3$; H, OCH$_2$Oalkyl; H, OCH(Oalkyl)CH$_3$; or H, OCH$_2$aryl;

with an imine of formula (III)

(III)

wherein
R[7] is —OH, —OCH$_3$ or —O—protective group; and
R[8] is R[2], CH$_2$N[Si(alkyl)$_o$(aryl)$_p$]CO$_2$CH$_2$(C$_6$H$_5$), CH$_2$N[Si(alkyl)$_o$(aryl)$_p$]CO$_2$tert-butyl, CH$_2$N=CH(C$_6$H$_5$), CH$_2$N=CH(C$_6$H$_4$-pOCH$_3$), CH$_2$N=CH[C$_6$H$_4$(R[4])] or (structure with Si-CH$_2$N-Si ring)

to give a compound of formula (IV)

(IV)

(b) hydrolyzing the compound of formula (IV) to give a compound of formula (V)

(V)

wherein R[9] is H;
(c) optionally converting the compound of formula (V) wherein R[9] is H into a compound of formula (V) wherein R[9] is (C$_1$-C$_4$)alkyl, CO(C$_1$-C$_4$)alkyl, COO(C$_1$-C$_4$)alkyl, or SO$_2$aryl, or into a corresponding anhydride;
(d) cyclizing the compound of formula (V) wherein R[9] is H, (C$_1$-C$_4$)alkyl, CO(C$_1$-C$_4$)alkyl, COO(C$_1$-C$_4$)alkyl, or SO$_2$aryl, or the anhydride to give a lactam of formula (VI)

(VI)

(e) optionally deprotecting the compound of formula (VI) wherein
Y is H, O-acetyl; H, OSi(alkyl)$_o$(aryl)$_p$ wherein o and p are independently 0, 1, 2 or 3, and o+p is 3; H, O-tetrahydropyranyl; H, OC(aryl)$_3$; H, OCH$_2$Oalkyl; H, OCH(Oalkyl)CH$_3$; or H, OCH$_2$aryl; or
R[7] is —O—protective group; or
R[8] is CH$_2$N[Si(alkyl)$_o$(aryl)$_{p]CO2}$CH$_2$(C$_6$H$_5$), CH$_2$N[Si(alkyl)$_o$(aryl)$_{p]CO2}$tert-butyl, CH$_2$N=CH(C$_6$H$_5$), CH$_2$N=CH(C$_6$H$_4$-pOCH$_3$), CH$_2$N=CH[C$_6$H$_4$(R[4])] or (structure with Si-CH$_2$N-Si ring)

to give the compound of formula (I) wherein R[2] is F, CH$_2$CH$_3$, or CH$_2$NH$_2$; and
(f) optionally reacting the compound of formula (I) wherein R[2] is CH$_2$NH$_2$ with a compounds of formula (XV) or (XVI)

(XV)

(XVI)

to give the compound of the formula (I) wherein R[2] is CH$_2$NHR[4]; and R[4] is H, CO—(CH$_2$—)$_n$CO—R[5], or CO—(CH$_2$—)$_n$NHR[6].

2. The process as recited in claim 1, wherein the compounds of formula (II) wherein Y is H; OH; is prepared by:
reducing 5-phenyl-5-oxopentanoic acid or methyl ester thereof to give 5-phenyl-5-hydroxypentanoic acid or methyl ester thereof; and
reacting the 5-phenyl-5-hydroxypentanoic acid or methyl ester thereof with (+)-(1S,2S)-pseudoephedrine (X).

3. The process according to claim 1, wherein Y is H, OH.

4. The process according to claim 1, wherein Y is H, O-acetyl; H, OSi(alkyl)$_o$(aryl)$_p$; H, O-tetrahydropyranyl; H, OC(aryl)$_3$; H, OCH$_2$Oalkyl; or H, OCH(Oalkyl)CH$_3$.

5. The process according to claim 2, wherein the reduction of 5-phenyl-5-oxopentanoic acid or methyl ester is carried by (R)-tetrahydro-1-methyl-3,3-diphenyl-1H,3H)-pyrrolo[1,2-C][1,3,2]oxazaborolidine reduction, Ru(II)-catalyzed asymmetric hydrogenation or chirally complexed Cu(I) hydride-catalyzed enantioselective hydrosilylation.

6. A compound of formula (II)

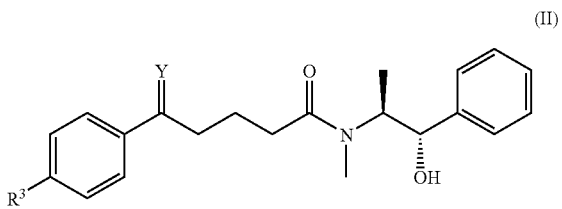

wherein:
R³ is H or F; and
Y is H, OH; H, O-acetyl; H, OSi(alkyl)$_o$(aryl)$_p$ wherein o and p are, independently 0, 1, 2 or 3, and o+p is 3; H, O-tetrahydropyranyl; H, OC(aryl)$_3$; H, OCH$_2$Oalkl; H, OCH(Oalkyl)CH$_3$; or H, OCH$_2$aryl.

7. A compound of formula (IV)

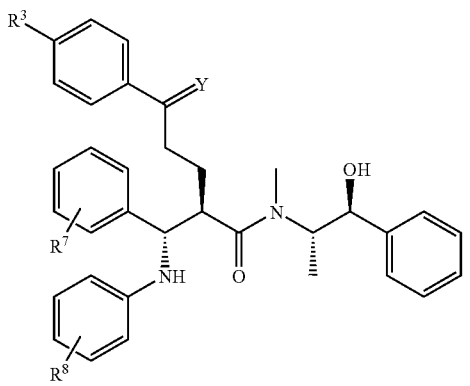

wherein:
R³ is H or F;
R⁷ is —OH, —OCH$_3$ or —O—protective group;
R⁸ is F, CH$_2$CH$_3$, CH$_2$NHR⁴, CH$_2$N[Si(alkyl)$_o$(aryl)$_p$]CO$_2$CH$_2$(C$_6$H$_5$), CH$_2$N[Si(alkyl)$_o$(aryl)$_p$]CO$_2$tert-butyl, CH$_2$N=CH(C$_6$H$_5$), CH$_2$N=CH(C$_6$H$_4$-$_p$OCH$_3$), CH$_2$N=CH[C$_6$H$_4$(R⁴)] or

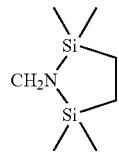

R⁴ is H, CO—(CH$_2$—)$_n$CO—R⁵ or CO—(CH$_2$—)$_n$NHR⁶;
R⁵ is OH, or NH—CH$_2$—[CH(OH)—]$_m$CH$_2$OH;
R⁶ is H or CO—[CH(OH)—]$_m$CH$_2$OH;
n is an integer from 4 to 16;
m is an integer from 1 to 5; and
Y is H, OH; H, O-acetyl; H, OSi(alkyl)$_o$(aryl)$_p$ wherein o and p are, independently, 0, 1, 2 or 3 and o+p is 3; H, O-tetrahydropyranyl; H, OC(aryl)$_3$; H, OCH$_2$Oalkyl; H, OCH(Oalkyl)CH$_3$; or H, OCH$_2$aryl.

* * * * *